(12) United States Patent
Holst et al.

(10) Patent No.: US 6,497,680 B1
(45) Date of Patent: Dec. 24, 2002

(54) METHOD FOR COMPENSATING FOR PRESSURE DIFFERENCES ACROSS VALVES IN CASSETTE TYPE IV PUMP

(75) Inventors: Peter A. Holst, Castro Valley, CA (US); David A. Krajewski, Hollister, CA (US); Rudolph J. Maske, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/464,812

(22) Filed: Dec. 17, 1999

(51) Int. Cl.⁷ .................................................. A61M 1/00
(52) U.S. Cl. ........................................ 604/153; 604/67
(58) Field of Search ..................... 604/65–67, 151–153, 604/132; 128/DIG. 12, DIG. 13; 417/53, 63, 282–285, 474, 477.2

(56) References Cited

U.S. PATENT DOCUMENTS

| | | |
|---|---|---|
| 3,966,358 A | 6/1976 | Heimes et al. |
| 4,278,085 A | 7/1981 | Shim |
| 4,322,201 A | 3/1982 | Archibald |
| 4,360,019 A | 11/1982 | Portner et al. |
| 4,411,651 A | 10/1983 | Schulman |
| 4,468,222 A | 8/1984 | Lundquist |
| 4,479,760 A | 10/1984 | Bilstad et al. |
| 4,583,981 A | 4/1986 | Urquhart et al. |
| 4,710,106 A | 12/1987 | Iwata et al. |
| 4,840,542 A | 6/1989 | Abbott |
| 4,842,584 A | 6/1989 | Pastrone |
| 4,845,487 A | 7/1989 | Frantz et al. |
| 4,927,411 A | 5/1990 | Pastrone et al. |
| 4,976,687 A | 12/1990 | Martin |
| 5,108,367 A | 4/1992 | Epstein et al. |
| 5,116,203 A * | 5/1992 | Natwick et al. ........ 604/153 X |
| 5,237,309 A | 8/1993 | Frantz et al. |
| 5,292,306 A | 3/1994 | Wynkoop et al. |
| 5,295,967 A | 3/1994 | Rondelet et al. |
| 5,336,051 A | 8/1994 | Tamari |
| 5,342,298 A | 8/1994 | Michaels et al. |
| 5,415,528 A | 5/1995 | Ogden et al. |
| 5,423,759 A | 6/1995 | Campbell |
| 5,554,115 A * | 9/1996 | Thomas et al. ........... 604/67 X |
| 5,586,868 A | 12/1996 | Lawless et al. |
| 5,626,563 A | 5/1997 | Dodge et al. |

(List continued on next page.)

*Primary Examiner*—Anhtuan T. Nguyen
(74) *Attorney, Agent, or Firm*—Beth A. Vrioni

(57) ABSTRACT

A pump used to infuse a fluid into a patient is controlled in accordance with an algorithm that enables a microprocessor to monitor and adjust each pump cycle to compensate for a differential pressure between the pump's inlet and outlet. The algorithm defines a fluid delivery protocol that is applied in controlling the operation of the pump to achieve a desired rate, volume, and timing of the fluid infusion. Fluid is delivered by the pump when a plunger compresses an elastomeric membrane overlying a fluid chamber. Due to the small volume of the chamber, an incremental change in the plunger position before the delivery stroke produces a significant change in the delivery pressure. At the beginning of a pump cycle, the microprocessor determines the differential pressure between the inlet and outlet of the pump, and adjusts the plunger position before the delivery stroke to compensate for the differential pressure. A retraction of the plunger from the home position decreases the delivery pressure of the fluid, and an advancement of the plunger increases it. After the position of the plunger is adjusted to compensate for the differential pressure, the pump cycle proceeds. Following the plunger stroke, the outlet pressure is used to determine the actual volume of fluid delivered. The duration of the plunger stroke in the next pump cycle is adjusted to compensate for any volume delivery error produced by the differential pressure compensation.

17 Claims, 10 Drawing Sheets

U.S. PATENT DOCUMENTS

| | | |
|---|---|---|
| 5,628,731 A | 5/1997 | Dodge et al. |
| 5,634,896 A | 6/1997 | Bryant et al. |
| 5,658,133 A | 8/1997 | Anderson et al. |
| 5,718,569 A | 2/1998 | Holst |
| 5,807,322 A | 9/1998 | Lindsey et al. |
| 5,810,770 A | 9/1998 | Chin et al. ............... 604/65 |
| 5,814,004 A | 9/1998 | Tamari |
| 5,816,779 A | 10/1998 | Lawless et al. |
| 5,882,339 A | 3/1999 | Beiser et al. |
| 5,989,222 A | 11/1999 | Cole et al. |

* cited by examiner

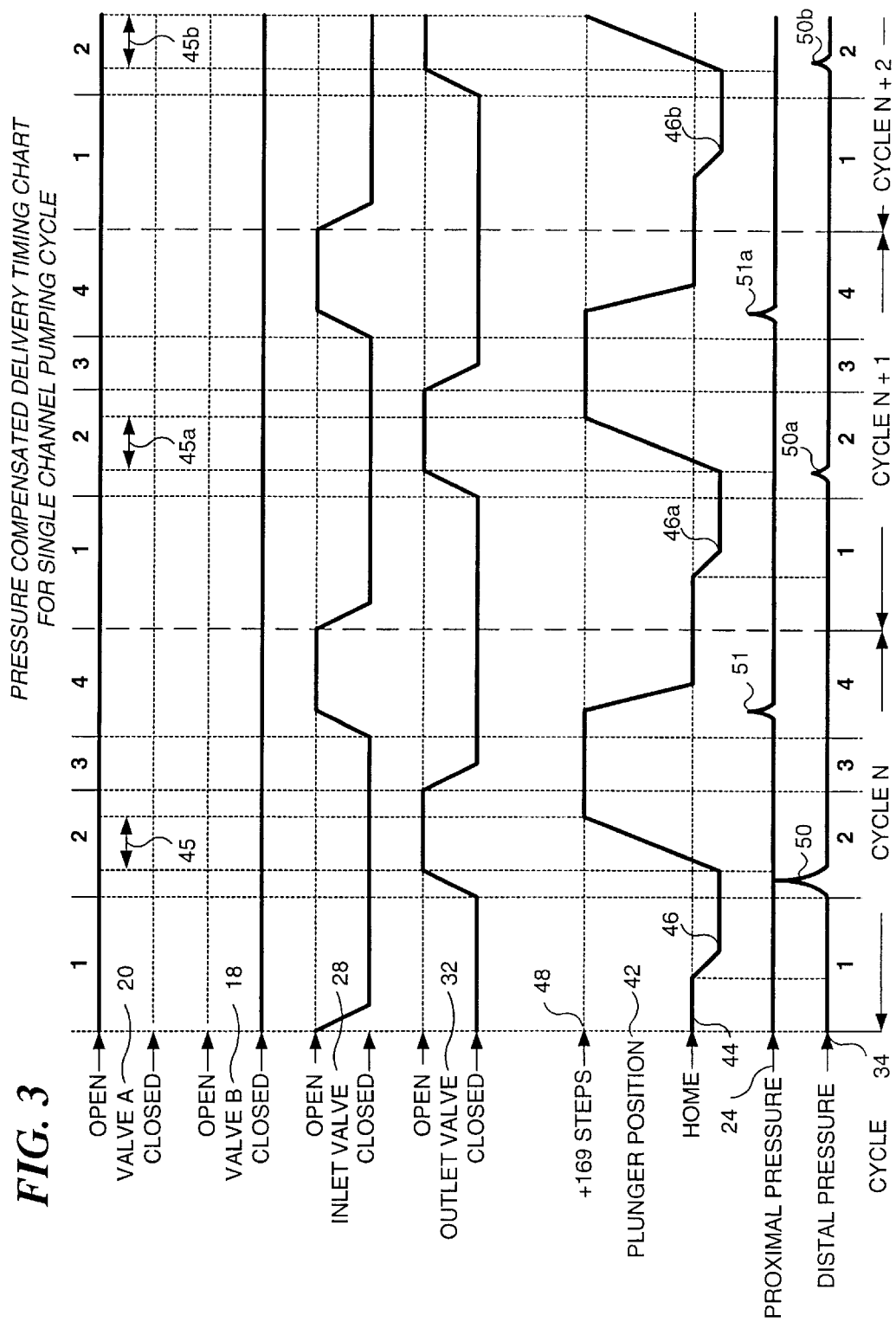

METHOD FOR COMPENSATING FOR PRESSURE DIFFERENCES ACROSS VALVES IN CASSETTE TYPE IV PUMP

FIELD OF THE INVENTION

The present invention generally relates to a method and apparatus used for compensating pressure differences between an inlet and outlet of a pump, and more specifically, to a method and apparatus for compensating pressure differences across the inlet and the outlet of a cassette type infusion pump used to deliver medicinal fluids intravascularly.

BACKGROUND OF THE INVENTION

Various types of pumps are used by medical personnel to infuse drugs into a patient's body. Of these, cassette infusion pumps are often preferred because they provide a more accurately controlled rate and volume of drug infusion than other types of infusion pumps. A cassette pump employs a disposable plastic cassette coupled in a fluid line extending between a drug reservoir and the patient's body.

In one prior art design of a cassette infusion pump, the cassette comprises a plastic shell or housing having a front section joined to a back section. A thin elastomeric sheet or membrane is encapsulated between the two sections. Fluid flows from one of two selectable inlet ports into a pumping chamber defined by a concave depression in one of the sections through passages formed in the housing. The cassette is inserted into an appropriate receptacle of a pump chassis that includes a microprocessor controller and a motor actuated driver. A plunger actuated by the motor in the pump driver displaces the elastomeric membrane to force fluid from the pumping chamber toward an outlet port under pressure. The pump chassis thus provides the driving force that pumps fluid through the cassette. The microprocessor control is programmable to deliver a selected volume of fluid to the patient at a selected rate of flow. In addition, the pump chassis may include one or more pressure sensors and air bubble sensors used to monitor the drug infusion process to protect against potential problems that may arise during the drug delivery.

Both single and multi-channel cassette pumps are available. A multi-channel cassette pump allows more than one type of medicinal fluid to be selectively delivered to a patient using a single pump cassette. Such pumps are frequently used in association with intravenous (IV) drug delivery therapies.

When the pump inlet and outlet pressure conditions are approximately equal, cassette type infusion pumps are quite accurate. However, when the pressures at the pump inlet and outlet vary substantially, the delivery accuracy of cassette pumps degrade. If the delivery rate is relatively low, as is often the case in pediatric applications, and if the differential pressure exceeds 3 psi, accuracy is significantly impaired, and retrograde flow can occur. In retrograde flow, fluid moves from the patient's vascular system towards the pump, which can result in blood from a patient being drawn out of the patient's body and into the IV line. Even if such retrograde flow occurs only briefly, and the accuracy of the delivery rate is not severely impaired, the visual impact of even a small amount of blood in an IV line can be extremely disturbing to care providers, patients, and visitors. Retrograde flow is more likely to occur if the pump fluid source is lower in elevation than the entry site of an IV line into the patient's body, because the inlet pressure is then lower than the outlet pressure due to the head pressure.

The effect that a differential pressure has on the accuracy of the flow rate of a cassette pump depends on whether the pressure at the pump inlet is higher or lower than the pressure at the pump outlet. A higher pump inlet pressure, which is typically due to an increased elevation of the fluid reservoir relative to the pump (i.e., the reservoir head pressure), often causes the flow rate to exceed the desired setting, which the pump is programmed to deliver. Conversely, a higher pump outlet pressure, which can be caused by a partially restricted fluid line connected to the pump outlet or by the entry site into the patient being disposed higher than the pump inlet, can cause the flow rate to decrease below the desired value.

In a balanced pressure environment, cassette pumps tend to act like constant displacement pumps, so that each pumping cycle delivers the same volume of fluid. The delivery rate of the fluid is controlled by varying the number of pumping cycles per unit of time; thus, higher delivery rates require more pumping cycles to be executed during a given time interval than lower delivery rates. The pumping cycle of the prior art cassette pump briefly described above corresponds to a plunger deflecting the elastomeric membrane into the chamber in which the constant volume of fluid is contained, thereby forcing the fluid from the chamber through an outlet valve. The position of the plunger is controlled by a microprocessor. It is possible to change the delivery pressure of the constant volume of fluid to be delivered into the fluid line that is coupled to the patient's body by adjusting the position of the plunger at the beginning of each pumping cycle. Because the fluid volume delivered during each cycle (and hence the volume of the chamber in which the fluid is contained) is relatively small (generally about 333 $\mu$l of fluid is delivered per cycle), a very small change in the initial plunger position will have a significant impact on the pumping chamber pressure.

Clearly, it would be desirable to provide a cassette pump in which a pressure compensated pumping cycle is used to minimize the effect of differential pressures between the inlet and outlet of the pump. A cassette pump achieving this benefit and having accurate flow rates under varying pressure conditions is not disclosed in the prior art. Preferably, such a system would use a multi-component pressure-kinetic model to determine the pressure compensation required due to a differential pressure between the inlet and outlet of the cassette pump. Such a system would preferably use real-time measurements of pressure at both the pump inlet and pump outlet to determine the differential pressure, and then use an empirically determined algorithm to determine the extent to which the position of the plunger should be adjusted to either increase or decrease the delivery pressure. The delivery rate can further be optimized by changing the rate of the pumping cycles as a function of the actual volume delivered during each pump cycle. Preferably such a model would be used to pressure compensate the delivery of medicinal fluids for single or multi-channel cassette pumps. It will thus be apparent that accurately controlling the administration of medicinal fluids under varying pressure conditions using a pressure compensation model would provide significant advantages over the prior art.

SUMMARY OF THE INVENTION

In accord with the present invention, a pressure compensated pump is defined for maintaining an accurate delivery of fluid to a patient when a differential pressure exists between an inlet and outlet of the pump. The pump includes a fluid drive unit that is adapted to couple with a fluid line and to force fluid from a source for infusion into the patient through the fluid line. A control unit is coupled to the fluid drive unit to control its operation. A first pressure sensor monitors the inlet pressure to the pump, and a second pressure sensor monitors the outlet pressure of the pump. Both the first and the second pressure sensors are electrically coupled to the control unit. The control unit is programmed to determine a differential pressure between the inlet and the outlet of the pump, and the control unit uses an algorithm stored in a memory to determine a correction factor to be applied to compensate for the differential pressure between the inlet and the outlet, thus ensuring accurate delivery of the fluid to the patient. In addition to correcting for pressure differences across the valves of the pump, the algorithm can include a correction factor that compensates for calibration differences between multiple pressure sensors, as well as a correction factor that compensates for differences between targeted intake fluid volumes and an actual intake fluid volumes, as well as for differences between targeted delivery fluid volumes and actual delivery fluid volumes.

Preferably, the control unit includes a microprocessor responsive to program steps stored in a memory included in the control unit. The pump includes a user interface coupled to the control unit to enable an operator to enter at least one parameter for controlling the delivery of the fluid to the patient, corresponding to either a rate of fluid flow, a volume of fluid flow, a time of fluid flow, and/or a duration of fluid flow.

Also preferably, the correction factor changes a delivery pressure of the fluid, and/or a duration of time between successive cycles of the pump. The algorithm used to determine the correction factor is empirically determined. In a preferred embodiment, the fluid drive unit includes an elastomeric membrane overlying a chamber in the pump. The chamber is in fluid communication with the source and the patient. A driven member that is coupled to a motor exerts a force on the elastomeric membrane, displacing it into the chamber, thereby causing fluid to be expelled from the chamber into the patient. The correction factor determined by the algorithm is expressed as a position of the driven member relative to the elastomeric membrane. In this embodiment, the corrected position of the driven member relative to the elastomeric membrane that is determined by the algorithm corresponds to a corrected position for the driven member at the start of a pump cycle, i.e., before the driven member exerts the force on the elastomeric membrane that causes the fluid to be expelled from the chamber into the patient.

When the control unit determines that the pressure at the outlet of the pump is greater than the pressure at the inlet, the control unit advances the driven member into the chamber to a position determined by the algorithm, and when the control unit determines that the pressure at the outlet is lower than the pressure at the inlet, the control unit retracts the driven member away from the chamber to a position determined by the algorithm. In either case, the driven member is always in contact with the elastomeric membrane during any segment of a pump cycle.

The algorithm employs a first lookup table in which a first value is indicated as a function of a pressure measured by the sensor monitoring the inlet pressure, and a second lookup table in which a second value is indicated as a function of a pressure measured by the sensor monitoring the outlet pressure. The correction factor is determined by combining the first value and the second value obtained from the first and second lookup tables. The lookup tables are preferably empirically determined. The algorithm preferably uses a pressure measured by the sensor monitoring the outlet pressure after the driven member has exerted a force on the elastomeric membrane and the fluid has been displaced and forced into the fluid line toward the patient, in determining the correction factor for the next pump cycle.

After the driven member has exerted a force on the elastomeric membrane and the fluid is forced from the chamber, the control unit uses the algorithm to determine the actual fluid volume delivered to the patient, and then calculates a correction factor that determines how the timing of the next pump cycle is to be modified to maintain a desired delivery rate of the fluid to the patient. The pump preferably includes an inlet valve and an outlet valve.

The correction factor that corresponds to a difference between a targeted intake fluid volume, and an actual intake fluid volume is determined by sampling a first pressure proximate the inlet port after the chamber has been filled with the targeted intake volume by moving the driven member to a first position, and then moving the driven member to a second position, such that the volume of the chamber is decreased. The inlet pressure sensor determines a second pressure proximate the inlet port that exceeds the first pressure proximate the inlet port by a predetermined amount. The algorithm determines the actual intake fluid volume as a function of the first pressure proximate the inlet port, the second pressure proximate the inlet port, the first position of the driven member, and the second position of the driven member; and determines a difference between the targeted intake fluid volume and the actual intake fluid volume. Preferably, the predetermined amount is about 1 psi. The difference between the targeted intake fluid volume and the actual intake fluid volume is used to increase the accuracy of the fluid infusion by adding the difference between the targeted intake fluid volume and the actual intake fluid volume to a targeted intake fluid volume of a subsequent pump cycle. Preferably, the functional relationships between the intake fluid volume, the proximate pressure, and the position of the driven member are empirically determined.

The algorithm can compensate for calibration differences between an inlet pressure sensor and an outlet pressure sensor. The steps employed to accomplish this function include opening the inlet valve while the outlet valve is closed, thus filling the pumping chamber with fluid, and closing the inlet valve when the chamber is filled with a desired volume of fluid. The next step determines a pressure proximate the inlet port and a pressure proximate the outlet port using the inlet and outlet pressure sensors. A position of the elastomeric membrane is adjusted such that a pressure of the fluid within the chamber is equivalent to the pressure proximate the outlet port; and the outlet valve is then opened. Next, the outlet pressure sensor is used to determine if a pressure spike accompanies the opening of the outlet valve (the pressure spike being indicative of a calibration difference between the inlet pressure sensor and the outlet pressure sensor). The pressure spike is used by the algorithm to compensate for the calibration difference in the next pump cycle.

In an alternate embodiment, the pump includes only a pressure sensor in fluid communication with an outlet side of the pump, and a first pump cycle is uncompensated. Two outlet pressure readings are taken during each cycle—one at a beginning of the pump cycle when the chamber is full of fluid, and one just as the fluid is finishing being expelled from the chamber. In the next pump cycle, the position of the driven member is adjusted relative to the chamber to compensate for any differential pressure between the two readings taken in the previous pump cycle.

Another aspect of the present invention is directed to a method that includes steps generally consistent with the functions implemented by the components of the apparatus described above. A further aspect of the present invention is directed to an algorithm that includes steps also generally consistent with the description set forth above.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 3 is a valve cycle diagram for a pressure compensated single channel pump, in accord with the present invention;

DETAILED DESCRIPTION OF THE PREFERRED EMBODIMENT

Overview of the Present Invention

Figure 1:
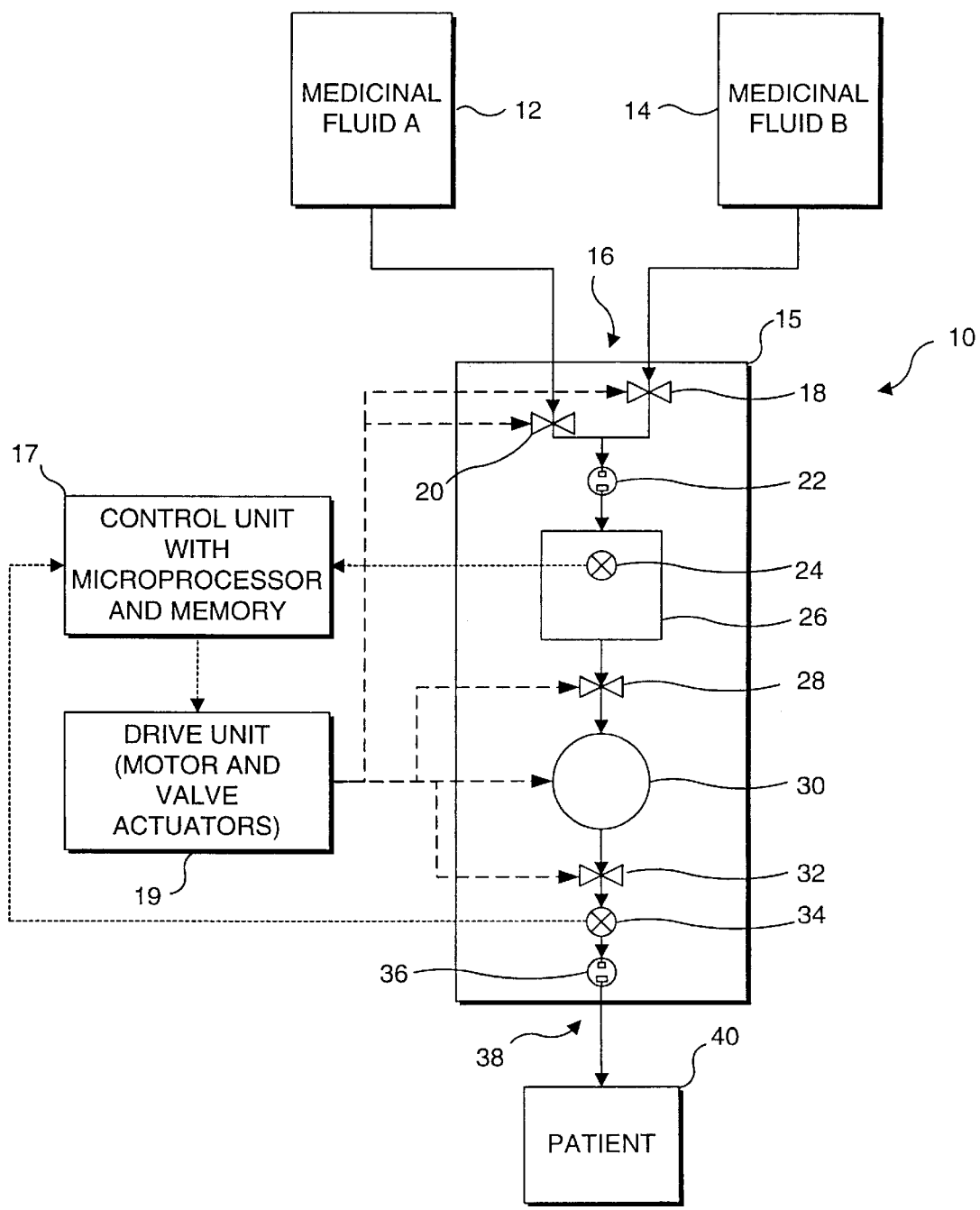
FIG. 1 is a schematic block diagram of a multi-channel, pressure compensated cassette pump in accord with the present invention.

The present invention employs an algorithm to compensate for a differential pressure between the inlet and outlet of a cassette type infusion pump to enhance the accuracy of the pump, particularly at low flow rates. A preferred embodiment of the present invention will be incorporated in Abbott Laboratories' PLUM A+™ Infusion Pump, which will be used in conjunction with its PLUM™ Cassette. The algorithm used in this embodiment has been empirically determined for these specific products. However, it should be noted that a similar algorithm can be empirically determined for other designs of infusion cassettes and infusion pumps. The present invention is thus not in any way limited to the specific design of the pump and cassette discussed below.

The terms "proximal" and "inlet" as used herein in connection with the following description and the claims that follow synonymously refer to the portion of the cassette that is coupled in fluid communication with a fluid line (or lines) adapted to be coupled to a fluid supply or reservoir of fluid. The terms "distal" and "outlet" similarly synonymously refer to the portion of the cassette that is coupled in fluid communication with a fluid line adapted to be connected to a patient.

Since the following description of a preferred embodiment of the present invention relates to its use with the PLUM A+ Pump and PLUM Cassette, certain aspects are determined by its operating specifications. For example, a deliverable volume per pump cycle in this embodiment is from 0–500 $\mu l$, with a preferred volume being about 333 $\mu l$. The uncompensated delivery rate is variable from 0–999 ml/hr, and the compensated delivery rate is variable from 0.1–500 ml/hr. The range of operable distal and proximal pressures is about −11.0 psi to 14.0 psi. In general, the pressure sampling occurs for about 2 ms/sample, over approximately a 50 ms sampling period. The plurality of samples are averaged to minimize any pressure sensing variations.

This embodiment of the present invention provides for monitoring the distal (outlet) and proximal (inlet) pressures of the pump cassette, determining the differential pressure between the two, and adjusts the pumping cycle to compensate for this differential pressure. The pumping cycle is adjusted by increasing or decreasing the pressure of the medicinal fluid within the pump cassette, and if required, changing the timing of the pump cycle. Prior to the initiation of each pump cycle, the differential pressure is again determined. A correction factor is determined by the algorithm, and the pressure of the medicinal fluid within the pump cassette is adjusted accordingly. As the fluid leaves the pump cassette, its pressure is also used to determine the actual volume of fluid being delivered by the current pump cycle. This information is used by the algorithm to determine how the timing of the next pump cycle should be varied to achieve a desired flow rate. Preferably, the timing is changed by varying the duration of the delivery stroke of the pump. This pressure compensation process is repeated for each cycle. Further details of the preferred embodiment are as follows.

Details of a Preferred Embodiment

With reference to FIG. 1, a multi-channel cassette infusion pump 10 that implements the present invention is shown. A source 12 of medicinal fluid A and a source 14 of medicinal fluid B are both coupled in fluid communication with a proximal end 16 of a cassette 15. The flow of medicinal fluid A into the cassette is selectively controlled by a supply valve 20, and the flow of medicinal fluid B is selectively controlled by a supply valve 18. If cassette 15 is to be used to pump only one of these two medicinal fluid at a time, only the appropriate supply valve 18 or 20 is opened to select the medicinal fluid to be pumped. The selected medicinal fluid (or fluids) then flow(s) through an air sensor 22 and into a mixing chamber 26. The air sensor and mixing chamber are common features of cassette type infusion pumps. The purpose of the air sensor is to detect air bubbles that may be entrained in medicinal fluid A and/or B before the fluid is passed on into the pumping chamber and to the patient. Excess air bubbles entering a patient's bloodstream can cause an air embolism with potentially harmful consequences. A proximal (or inlet) pressure sensor 24 is disposed within mixing chamber 26. The selected medicinal fluid or fluids exit the mixing chamber through an inlet valve 28, when the inlet valve is in its open position, and into a pumping chamber 30. Details of suitable pressure sensors for use with the present invention and of other aspects of the cassette are disclosed in commonly assigned U.S. Pat. No. 5,554,115, the specification and drawings of which are hereby specifically incorporated herein by reference.

Cassette style infusion pumps are constant displacement pumps. The volume of medicinal fluid in chamber 30 is therefore generally the same for each pump cycle. The differential pressure between the proximal and distal sides of the cassette can be compensated by increasing or decreasing the pressure of the constant volume of fluid within pumping chamber 30, as appropriate. As noted above, the preferable delivery volume of the medicinal fluid contained within chamber 30 is 333 $\mu$l—for this particular embodiment. Because of the small volume of the chamber, only a very small change in the relative volume of chamber 30 is required to provide an increase or decrease in the pressure of the medicinal fluid within the chamber. One side of chamber 30 is covered with an elastomeric membrane 29. Medicinal fluid is forced from pumping chamber 30 (when inlet valve 28 is closed and an outlet valve 32 is opened), by the action of a plunger 42 (schematically shown in FIGS. 2A–2C) acting on the elastomeric membrane, forcing the elastomeric membrane into the chamber to displace the fluid contained therein. Adjusting the pressure within chamber 30 can easily be accomplished with an incremental change in the position of the plunger relative to the chamber before the start of a pumping cycle. In the preferred embodiment, the plunger position is variable from −489 steps to +220 steps, where a home position is defined to be at 0 steps. A nominal stroke distance for plunger 42 to deliver 333 $\mu$l of fluid is +169 steps.

Inlet valve 28 and outlet valve 32 are formed in the cassette and are closed when rods (not shown) driven by drive unit 19 act on the elastomeric membrane to close off flow through the fluid passage of the cassette. Details of this mechanism are not disclosed herein, but are well known to those of ordinary skill in this art. When outlet valve 32 is in its open position, the medicinal fluid forced from the chamber flows through past a distal pressure sensor 34, through a distal air sensor 36, and exits the cassette to be conveyed to a patient 40. Multi-channel infusion pump 10 also includes a control unit 17 and a drive unit 19. Control unit 17 preferably includes a microprocessor and a memory (not separately shown), however, it will be understood that the control unit can alternatively use other types of logic devices for implementing the algorithm, such a hardwired logic control, an application specific integrated circuit, etc. The algorithm is stored as a plurality of machine language instructions and data within the memory. The microprocessor receives information from distal pressure sensor 34 and proximal pressure sensor 24, and implements the algorithm to determine whether the plunger position should be advanced or retracted to compensate for the differential pressure (see FIGS. 2A–2C). Drive unit 19 includes a prime mover (an electrical motor—not specifically shown) that is drivingly coupled to plunger 42, which forces fluid from chamber 30.

The algorithm compensates for a differential pressure detected between proximal end 16 and a distal end 38 of the cassette pump primarily by changing the position of the plunger relative to chamber 30 to increase or decrease the pressure within the chamber before the actual pumping stroke occurs. The algorithm can also change the timing of the pump cycle by controlling drive unit 19. Further details of the algorithm are discussed below.

Figure 2A:
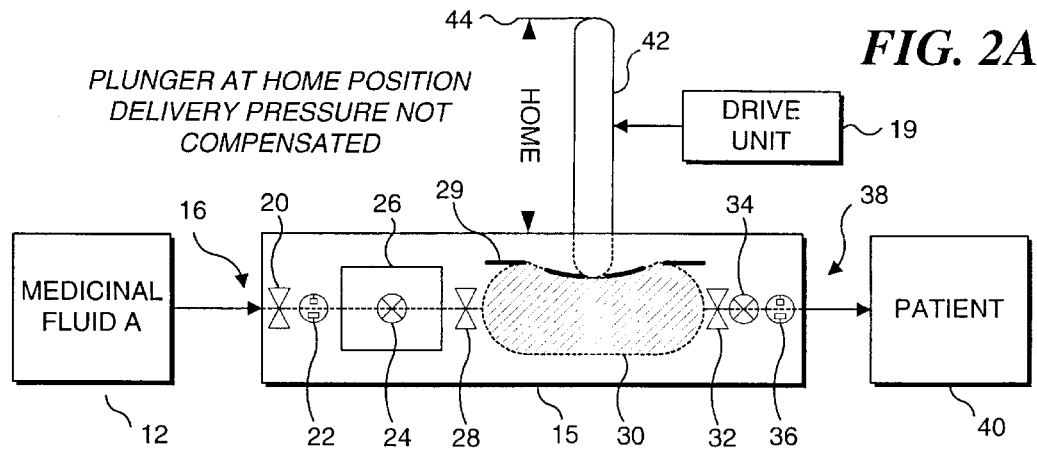
FIG. 2A is a schematic block diagram of the multi-channel pressure compensated cassette pump of FIG. 1, showing a driven plunger in a home (uncompensated) position relative to an elastomeric membrane covered pumping chamber, as would be appropriate when pressure compensation is not required.
Figure 2B:
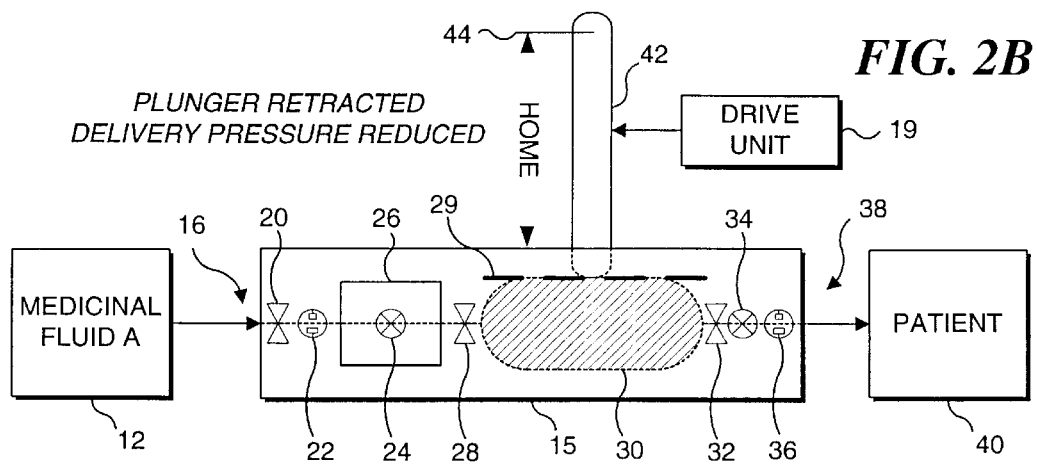
FIG. 2B is a schematic block diagram of the multi-channel pressure compensated cassette pump of FIG. 1, showing the driven plunger in a retracted (compensated) position relative to the elastomeric membrane covered pumping chamber, thus compensating for a proximal pressure that is greater than a distal pressure.
Figure 2C:
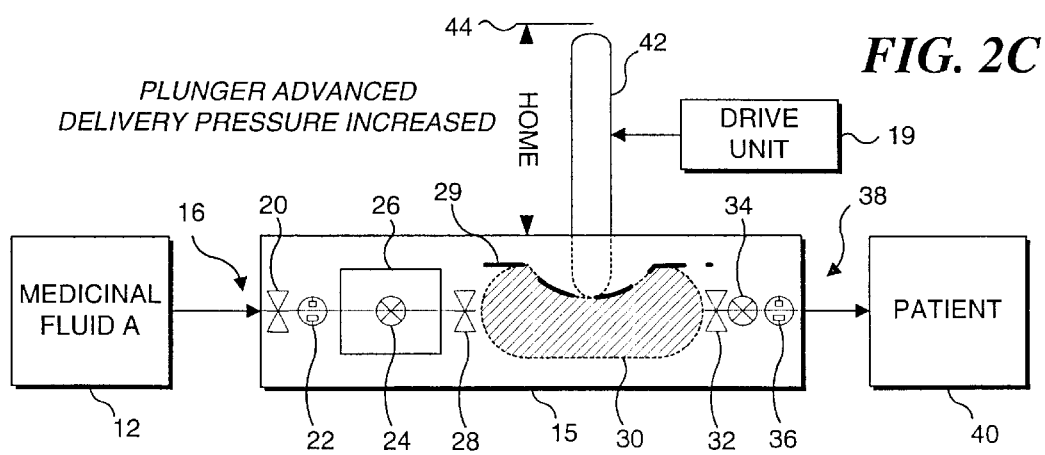
FIG. 2C is a schematic block diagram of the multi-channel pressure compensated cassette pump of FIG. 1, showing the driven plunger in an advanced position relative to the elastomeric membrane covered pumping chamber, thus compensating for a proximal pressure that is lower than a distal pressure.

FIGS. 2A–2C illustrate how a change in the position of the plunger relative to the chamber affects the volume of chamber 30, and thus the pressure of the fluid within the chamber during a pump cycle. For simplicity, only medicinal fluid A is shown in these figures. However it should be understood that alternatively, the present invention can be applied to compensate for a differential pressure of medicinal fluid B, or for a combination of medicinal fluid A and medicinal fluid B that is passing through multi-channel cassette infusion pump 10. In FIG. 2A, plunger 42 is shown in a home position (at the 0 step position). This position corresponds to the initiation of a pump cycle in which no differential pressure compensation is needed. Note that plunger 42 is in contact with the elastic membrane of pumping chamber 30, causing a slight deflection of the membrane. At the beginning of a pump cycle, plunger 42 is in an extend position at +169 steps, outlet valve 32 is closed, inlet valve 28 is open, and supply valve 20 is in the open position (for selection only of medicinal fluid A). Pumping chamber 30 is filled with the appropriate amount of medicinal fluid for the cassette pump, preferably about 333 $\mu$l for this embodiment, by retracting plunger 42.

When the algorithm determines that to properly compensate for a differential pressure, the delivery pressure must be reduced (i.e., because the proximal pressure is greater than the distal pressure), the plunger is retracted (while both inlet valve 28 and outlet valve 32 are closed) by the number of steps determined by the algorithm. Note that drive unit 19 preferably comprises a stepping motor (not separately shown), and it is therefore appropriate to refer to the displacement of plunger 42 in terms of steps of the stepping motor. FIG. 2B shows plunger 42 retracted to compensate for this differential pressure condition. Inlet valve 28 and outlet valve 32 are in their closed position, and it will be apparent that the volume of pumping chamber 30 has been increased (relative to its volume in FIG. 2A) due to the retraction of the plunger. Consequently, the pressure within pumping chamber 30 is effectively reduced before the plunger is displaced by the number of steps necessary to pump a nominal 333 $\mu$l of fluid.

Conversely, when the algorithm determines that the delivery pressure needs to be increased to compensate for the proximal pressure being lower than the distal pressure, the plunger is initially advanced into the chamber by an increment determined in accord with the algorithm. FIG. 2C clearly shows that when the plunger is in this advanced position, pressure chamber 30 has a reduced volume. Therefore, the pressure of the medicinal fluid within pumping chamber 30 will be increased under these conditions.

FIG. 3 provides details of a pumping cycle timing chart for multi-channel cassette pump 10 in which only a single medicinal fluid supply is being infused. While the infusion pump is being operated in this manner, supply valve 20 for medicinal fluid A is in its open position at all times, and supply valve 18 for medicinal fluid B is in its closed position at all times. Of course, it is also possible for a user to desire to deliver only medicinal fluid B, rather than medicinal fluid A, in which case the positions of the valves would be altered accordingly. As shown in FIG. 3, a single cycle of the cassette infusion pump has four separate parts when only a single medicinal fluid supply is being infused. In Part 1 of each pump cycle, inlet valve 28 is initially in its open position and then closes rapidly. Outlet valve 32 is in its closed position, and plunger 42 is initially in a home position 44. At this point, medicinal fluid A has filled chamber 30, and after the inlet valve closes, the chamber is isolated, so that any change in position of plunger 42 will affect the pressure of the fluid trapped within the chamber. Plunger home position 44 corresponds to the desired position of plunger 42 if the proximal and distal pressures are substantially equivalent (i.e., when no compensation is required).

Plunger 42 remains in home position 44 until the microprocessor in control unit 17 has received pressure readings from both proximal pressure sensor 24 and distal pressure sensor 34. Once the microprocessor in control unit 17 has received these pressure readings, the pressure readings are used by the algorithm stored in the memory of control unit 17 to determine any differential pressure between the two readings, and a correction factor is determined. This correction factor is expressed as a step change in the position of the plunger 42. In the exemplary pump cycle time chart illustrated in FIG. 3, it is assumed the algorithm has determined that the plunger is to be retracted to cause the delivery pressure to be reduced (as is illustrated in FIG. 2B). Once this correction factor has been determined, control unit 17 will cause drive unit 19 to retract the plunger the desired number of steps to a pressure compensated plunger position 46 (illustrated in Part 1 of FIG. 3). In this preferred embodiment, the maximum plunger extension is +229 steps from plunger home, and the maximum retract position is −220 steps from plunger home. The nominal delivery extension stroke for the plunger is +169 steps from plunger home. When the distal and proximal pressures are equal, the nominal plunger extension stroke of 169 steps will deliver the desired 333 µl of the selected medicinal fluid to the patient.

Preferably, the distal and proximal pressures used by the algorithm to determine the correct plunger position will be an average of multiple pressure readings. The following functional relationship converts a series of pressure data samples into an average pressure and filters out small variations in pressure. The Average Filter Pressure ($P_{Ave}$) transform is:

$$P_{Ave} = \frac{\sum_{n=0}^{7} P_{AT}(t = n \cdot 5 \text{ msec})}{8} \quad (1)$$

For Part 1, as inlet valve 28 is closing, the proximal pressure is preferably measured every motor step, and the Proximal Suspend Pressure is calculated by averaging the first 8 data samples using Equation (1).

An exception to the above equation exists when the pressure sensor is sampled once per motor step, which could differ from 5 msec. An alternate way to filter small variations from multiple pressure sample reading is to use an Exponential Filter Pressure transform. This functional relationship converts a series of pressure data samples into an exponential filter pressure ($P_{Filt}$). The Exponential Filter Pressure transform is:

$$P_{Filt}(n) = (1-\alpha) \cdot P_{Filt}(n-1) + \alpha \cdot P_{AT}(n) \quad (2)$$

where $0 < \alpha < 1.0$. The $\alpha$ coefficient is selected based on an expected settling time constant.

Figure 5:
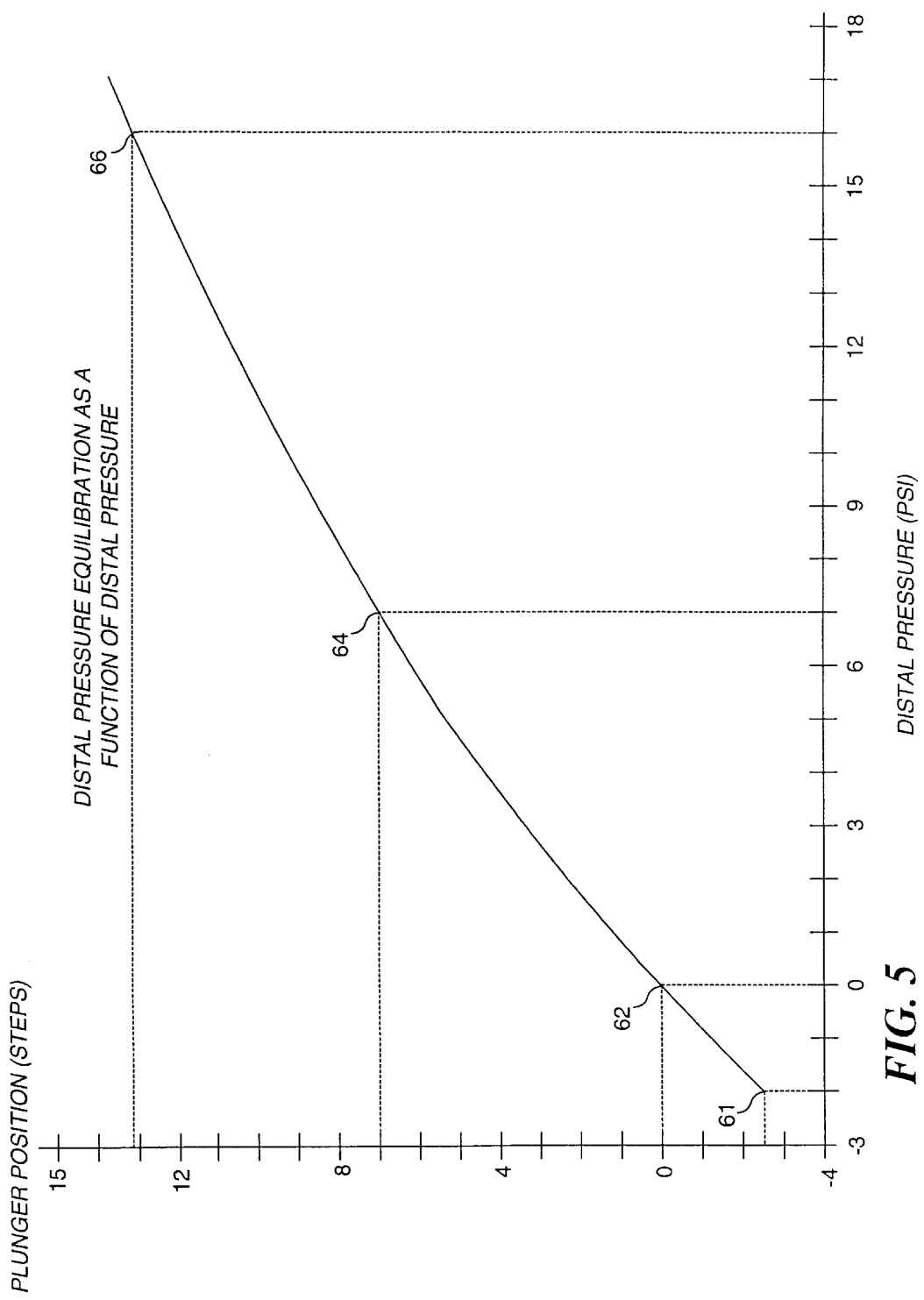
FIG. 5 is a graph showing the driven plunger position as a function of the distal pressure.
Figure 6:
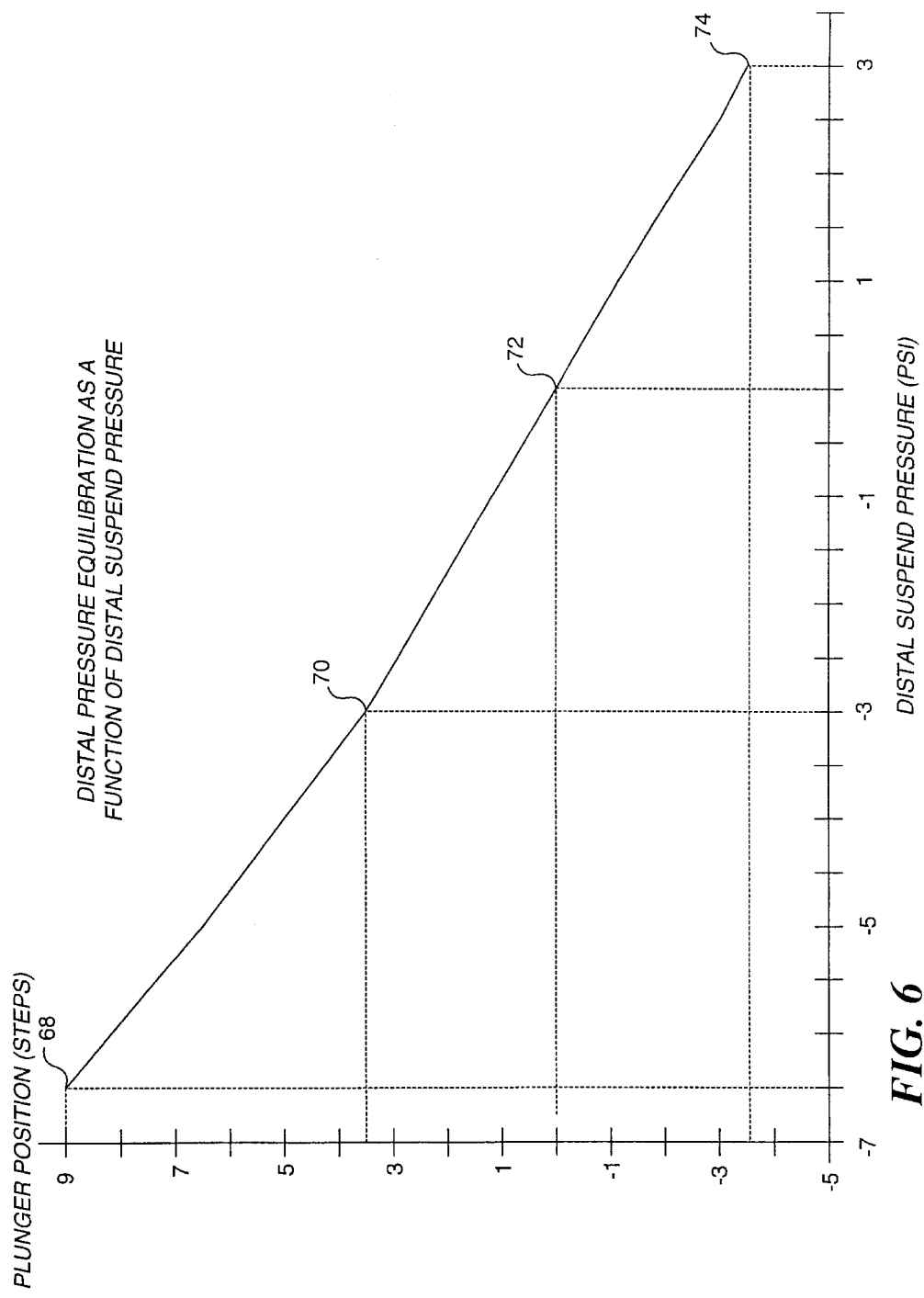
FIG. 6 is a graph showing the driven plunger position as a function of the distal suspend pressure (the proximal pressure calibrated relative to the distal pressure)

In Part 1 of FIG. 3, the pressure readings are input to the algorithm to determine the correct position adjustment for plunger 42. As noted above, the algorithm is empirically determined based on a particular type of cassette and pump to which the present invention is applied. FIGS. 5 and 6 are graphs showing empirically derived relationships specifically determined for the pump and cassette described above. The data shown in these graphs are preferably stored as lookup tables in the memory of control unit 17, and are thus available to be accessed by the microprocessor to be used in conjunction with the algorithm and the average pressure data as discussed above. Two lookup tables are required, as one lookup table expresses plunger position as a function of the average distal pressure, and the other lookup table expresses plunger position as a function of the average distal suspend pressure (a calculated equivalent of the proximal pressure, as will be described below).

FIG. 5 provides the correct number of steps that plunger 42 is to be moved based on a particular distal pressure reading and shows plunger 42 positioned as a function of the distal pressure. Note that a distal pressure reading of 0 psi corresponds to a data point 62, which in turn corresponds to a plunger position adjustment of 0 steps (as would be expected, no compensation is required for a 0 psi pressure). With reference to the graph of FIG. 5, if the distal pressure reading is 7 psi, the plunger position should be advanced 7 steps, as indicated by a data point 64. Likewise, if the distal pressure reading is 16 psi, the plunger position should be advanced slightly more than 13 steps; as indicated by a data point 66.

As noted above, the lookup table based on FIG. 5 must be used in conjunction with the lookup table based on FIG. 6, which shows the plunger position as a function of the Distal Suspend Pressure, to determine the corrected plunger position. In the first pump cycle, immediately after energizing the pump, the proximal pressure is used in determining the correction. Subsequent pump cycles use the Distal Suspend Pressure rather than the proximal pressure for this purpose, to avoid the effect of any calibration differences (or error) between proximal pressure sensor 24 and distal pressure sensor 34. For instance, in the first pump cycle, a distal pressure reading might be 5 psi, and a proximal pressure reading might 2 psi, yielding an apparent differential pressure of 3 psi. The algorithm will use both lookup tables (FIGS. 5 and 6) to determine the correct position for plunger 42 to compensate this differential pressure. It would be expected then, that after outlet valve 32 is opened, the distal pressure sensor would not record a pressure spike, since the differential pressure has been compensated. However, in practice, a pressure spike is often sensed by distal pressure sensor 34, indicating that some differential pressure still exists. The primary cause of this phenomenon is that the distal and proximal pressure sensors are slightly out of calibration relative to one another. For instance, a pressure spike of 1 psi indicates that the calibration of the distal and proximal pressure sensors disagree by 1 psi. So, after the initial pump cycle, the Distal Suspend Pressure, which incorporates a correction for the pressure spike seen after outlet valve 32 opens, is used.

The following functional relationships are used to determine the Distal Suspend Pressure ($P_{DxSus}$) for use with the data in FIG. 6. The first relationship is the transfer characteristic of the proximal pressure sensor reading ($P_{PxSus}$), which is calibrated to the Distal Suspend Pressure ($P_{DxSus}$), for the current cycle (n).

$$P_{DxSus}(n) = P_{PxSus}(n) + P_{DxAdj}(n) \quad (3)$$

In the first cycle, the Distal Suspend Pressure is set equal to the proximal pressure sensor reading ($P_{PxSus}$). For subsequent pump cycles, $P_{DxAdj}(n)$, which is the Distal Spike Amplitude, is required to solve Equation 3 to determine the Distal Suspend Pressure. The Distal Spike Amplitude can be obtained using the Distal Spike Amplitude transform. This functional relationship converts a series of pressure data samples into a representative spike amplitude. These pressure data samples are taken at the distal pressure sensor 34, during Part 2 of FIG. 3, and these values represent a Distal Pressure Spike 50 that occurs immediately after outlet valve 32 opens. Preferably, this spike is less than 0.5 psi in magnitude, in which case, the accuracy of the delivery rate will be acceptable. Especially during the first pump cycle, when the calibration differences between the distal and proximal pressure sensors have not been corrected, Distal Pressure Spike 50 is often greater than 0.5 psi. The baseline pressure is the average of the first few data points in the set used to establish the pre-disturbance pressure. The Distal Spike Amplitude ($P_{Dx\_Spk}$) transform, for the current cycle (n) is:

$$P_{Dx\_Spk}(n) = V_{Dx\_spk}(n) + 0.043 V \quad (4)$$

$$P_{DX\_Adj}(n) = \sum_{i=0}^{n-1} \frac{1 \text{ psig}}{0.020 \text{ V}} \cdot P_{Dx\_Spk}(i) = \sum_{i=0}^{n-1} \frac{50 \text{ psig}}{1 \cdot V} \cdot P_{Dx\_Spk}(i) \quad (5)$$

where:

$V_{Dx\_Spk}(n)$ is the Distal Spike Pressure measured approximately 100 msec after outlet valve 32 is opened;

0.020 V/psig is an empirically derived slope of the linear relationship between the spike voltage versus the sensor's offset pressure ($P_{Px}-P_{Dx}$); and 0.043V is the offset (in psig) of the linear relationship between the spike voltage versus the sensor's offset pressure ($P_{Px}-P_{Dx}$).

Thus, for FIG. 6, in the first pump cycle, the microprocessor of control unit 17 uses the proximal pressure reading (averaged per Equation 1 above) to determine the position correction for plunger 32. In subsequent cycles, the microprocessor of control unit 17 uses the Distal Suspend Pressure as calculated per the above equations. Note that a Distal Suspend Pressure reading of 0 psi corresponds to a data point 72 in FIG. 6, which in turn corresponds to a plunger position adjustment of 0 steps (since, as would be expected, no compensation is required for 0 psi pressure). If the Distal Suspend Pressure reading is −6.5 psi, the plunger position should be advanced 9 steps, as indicated by a data point 68 in FIG. 6. Likewise if the Distal Suspend Pressure reading is −3 psi, the plunger position should be advanced slightly more than 3.5 steps; as indicated by a data point 70. Again, it should be noted that FIG. 6 is empirically determined for the specific combination of pump and cassette used.

Returning now to Part 1 of FIG. 3, pressure compensated plunger position 46 is determined as will be further explained below, using the averaged pressure readings (per Equation 1) from distal pressure sensor 34, the lookup table based on the data of FIG. 5, averaged pressure readings (per Equation 1) from proximal pressure sensor 24, and the lookup table based on the data of FIG. 6. Note that for subsequent cycles, Equations 2, 3, and 4 are used to determine the Distal Suspend Pressure, which includes a correction factor for calibration differences between the distal and proximal pressure sensors, as described above.

Assuming that the average Distal Pressure reading was −2 psi, the corresponding plunger position correction would be approximately −2.5 steps, or a retraction of 2.5 steps from the home position. This relationship can be clearly seen by referring to data point 61 of FIG. 5. Further, assuming that the average Proximal Pressure reading was 3 psi, referring to data point 74 of FIG. 6, the corresponding plunger position correction would be approximately −3.5 steps, or a retraction of 3.5 steps from the home position. Combining these two corrections results in a net plunger position correction of −6 steps, or a retraction of 6 steps. Pressure compensated plunger position 46 in FIG. 3 is thus retracted from the home position by this amount. Such a retraction enables the elastomeric membrane to draw back from chamber 30, thus increasing the size of chamber 30, and decreasing the pressure of the medicinal fluid within the chamber. When outlet valve 32 is opened, the delivery pressure of the medicinal fluid will be reduced from what it would have been in an uncompensated pump cycle.

Because in this example, the proximal pressure is greater than the distal pressure, lowering the delivery pressure is a logical compensation. The relationship between the final corrected plunger position 46 and the lookup tables based on the data of FIGS. 5 and 6 can be described by the following equation:

$$X_{Dx\_EQ}(n) = TAB_{PxEq}(P_{DxSus}) + TAB_{DxEq}(P_{DxDel}) \quad (6)$$

Part 2 of the valve cycle timing illustrated in FIG. 3 starts when outlet valve 32 begins to open, at which time, distal pressure sensor 34 records a Distal Pressure Spike 50. The pressure is preferably sampled at 2 ms/sample, for 50 ms. These pressure samples are not averaged, as the peak pressure, not the average pressure, is desired. The Distal Spike Amplitude ($P_{DxSpk}$) transform is used (Equations (4) and (5)) to convert the distal pressure samples to a Distal Pressure Spike. Distal Pressure Spike 50 as shown in FIG. 3 is a positive pressure spike, but it could equally as well be a negative pressure spike. As noted above, this pressure spike is primarily caused by differences in the calibration of the distal and proximal pressure sensors. However, there are other causes of this pressure spike, including pressure fluctuations within the fluid lines leading to the patient or from the source to the cassette. At the beginning of Part 2, a Distal Pressure Spike 50 of 1.5 psi was recorded by distal pressure sensor 34, indicating that the distal pressure sensor and the proximal pressure sensor are mis-calibrated relative to each other by about 1.5 psi. This information is used during the next pump cycle, described above with respect to FIG. 6 and the equations relating to the Distal Suspend Pressure. As noted above, when the pressure spike measured in Part 2 of the pump cycle is less than 0.5 psi, then the accuracy of the medicinal fluid delivery will be acceptable.

Plunger 42 is moving in Part 2 of the pump cycle illustrated in FIG. 3. The plunger position is advanced to +169 steps, to a position 48. It should be noted that the actual movement of the plunger will not be 169 steps, but instead will be 169 steps plus the number of steps the plunger was retracted during Part 1 of the valve cycle (6 steps in the above example). If the plunger were advanced in Part 1 of the valve cycle, the actual distance the plunger will move will be 169 steps minus the number of steps the plunger was advanced. The +169 step position 48 represents the nominal stroke of the plunger that is required to deliver the 333 µl of medicinal fluid contained in chamber 30 when the proximal and distal pressures are in equilibrium. It should be noted that the time required for the plunger to move from pressure compensated plunger position 46 to the +169 steps of position 48 is a function of the pressure within the pumping chamber in the extended position of the previous cycle ($Tab_{EXT\_V}(P_{DxPC}[n-1])$), and the pressure of the pumping chamber in the home position ($Tab_{HOM\_V}(P_{DxSus})$).

The following functional relationship describes the required time, which is indicated as a time segment 45 in Part 2 of FIG. 3.

$$T_{Def} = f\{Tab_{Ext\_v}(P_{DxPC}[n-1]), Tab_{HOM\_v}(P_{Dx\_Sus})\} \quad (7)$$

A longer duration extend stroke of the plunger slows the delivery rate (note that the volume being delivered remains constant at 333 µl, plus or minus small variations). The timing change is calculated using the functional relationships and empirically determined lookup tables described below.

Figure 7:
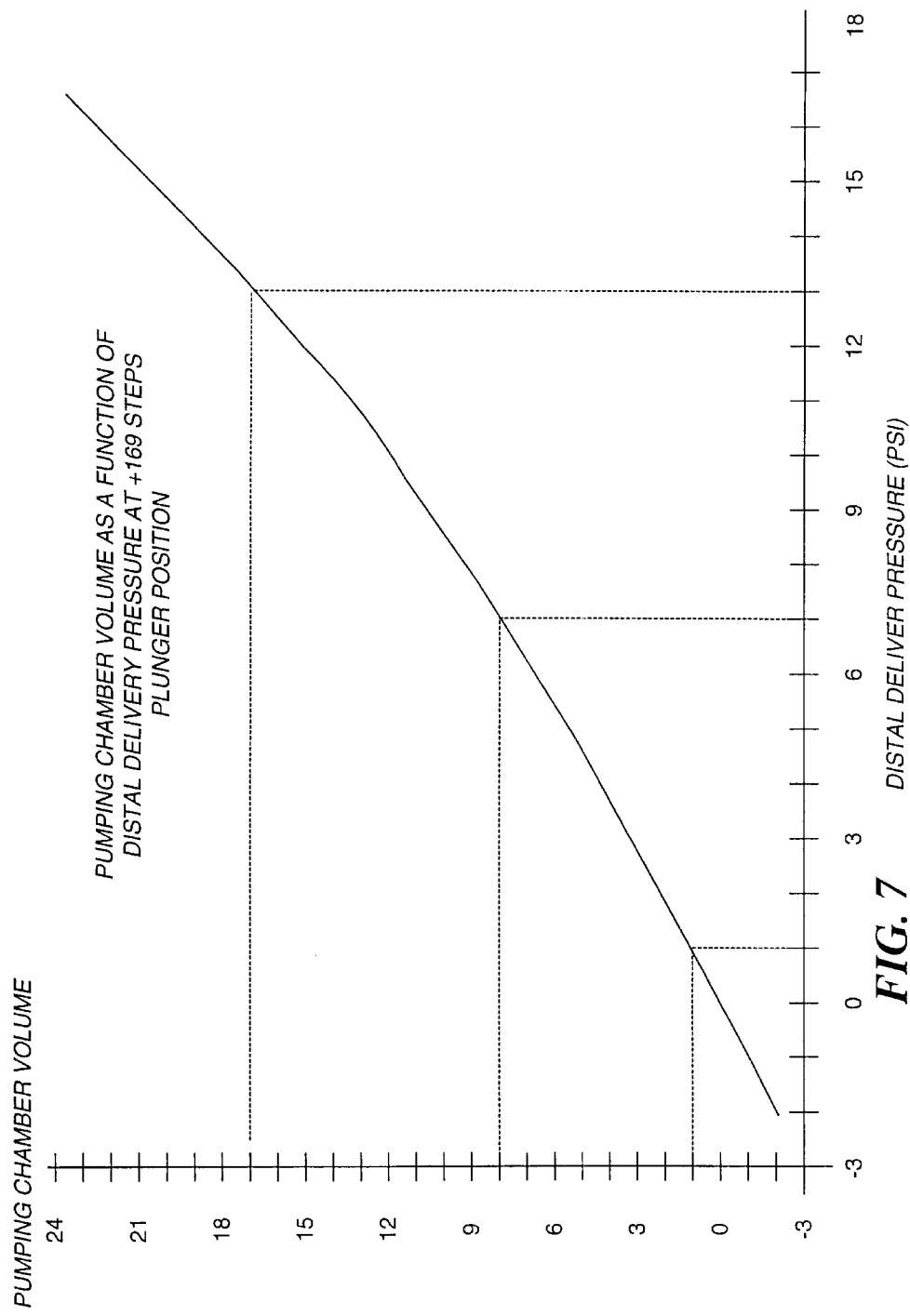
FIG. 7 is a graph showing the volume of the elastomeric pumping chamber with the driven plunger at the +169 step position as a function of the distal pressure.
Figure 8:
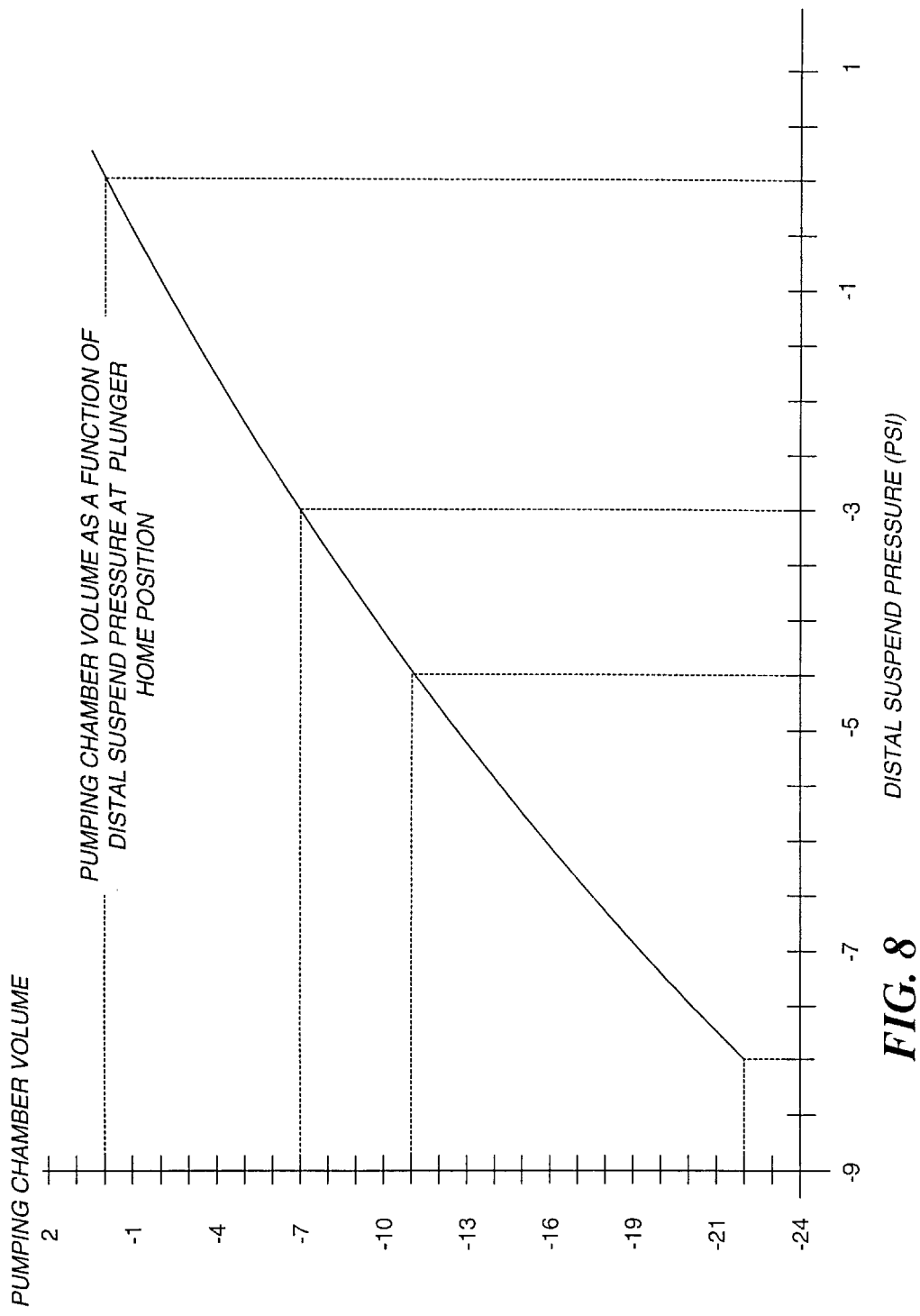
FIG. 8 is a graph showing the volume of the elastomeric pumping chamber with the driven plunger at the home position as a function of the distal suspend pressure.

An equilibrated plunger Extend Step Period is needed to deliver a stroke volume of fluid while maintaining an expected delivery rate, and the Equilibration Step Period transform is defined by the following equation (refer also to FIGS. 3 and 4, and time segments 45, 45a, and 45b):

$$T_{Step} = [T_{Ext}(n-1) - T_{Now} + A] \div [+169 \text{ steps} - X_{DxEq}] \quad (8)$$

$$A = [333 \, \mu l + TAB_{Hom\_v}(P_{DxSus}) + TAB_{Ext\_v}(P_{DxPC}[n-1])] \div R_{Del} \quad (9)$$

where:

$T_{Ext}(n-1)$ is the time stamp when the last cycle plunger extend stroke ended (+169 steps 48);

$T_{Now}$ is the time stamp of the current plunger position, just before extension of the plunger;

333 µl is the nominal plunger stroke volume at 0 psig;

$TAB_{Hom\_v}(P_{DxSus})$ is the value from the error volume lookup table (FIG. 8) at the plunger home position, as a function of proximal pressure (calibrated to the distal pressure);

$TAB_{Ext\_v}(P_{DxPC}[n-1])$ is the value from the error volume lookup table (FIG. 7) at +169 steps, as a function of distal pressure from the previous cycle;

$R_{Del}$ is the user specified delivery rate;

+169 steps is the nominal plunger extend position (+169 steps at position 48);

$X_{DxEq}$ is the plunger position, after equilibration and just before extension; and the plunger Extend Step Period, $T_{Step}$ is greater than 2 ms.

The expected delivery rate is maintained by keeping the time period $T_{Ext}(n) - T_{Ext}(n-1)$ constant. There are two plunger extend stroke error volume lookup tables ($TAB_{Hom\_v}$, based on the data shown in FIG. 8, and $TAB_{Ext\_v}$, based on the data shown in FIG. 7), which are functions of the pressure in the chamber, and relate to the time segment as described in Equation (7). The data for these two tables are derived empirically. The tables relate to differential pressures when inlet valve 28 is closed after an intake stroke ($P_{DxSus}$), and when the outlet valve 32 is closed after the extend stroke ($P_{DxPC}$) of the plunger. These two differential pressures occur at the plunger home position 44 and at the +169 steps, at position 48.

Based on the results of the above relationships, plunger 42 is moved to the extend position (the +169 step position) in the calculated time segment (time segments 45, 45a, 45b, etc.) As noted above, the pressure readings are also used to calculate parameters relating to the intake stroke of plunger 42. Following the extend stroke, the Actual Volume Delivered is computed. The Actual Volume Delivered is computed by using the following functional relationship:

$$333 \, \mu l + TAB_{Hom\_v}(P_{DxSus}) + TAB_{Ext\_v}(P_{DxPC}[n-1]) \quad (10)$$

where:

333 µl is the nominal plunger stroke volume at 0 psig;

$TAB_{Hom\_v}(P_{DxSus})$ is the value from the error volume lookup table (FIG. 8) at the plunger home position, as a function of proximal pressure (calibrated to the distal pressure); and $TAB_{Ext\_v}(P_{DxPC}[n-1])$ is the value from the error volume lookup table (FIG. 7) at +169 steps, as a function of distal pressure from the previous cycle.

Equation (10) is related to the Equilibration Step Period transform described above, as can be seen from Equation (9).

After the Actual Volume Delivered has been calculated as described above, the pump cycle advances to Part 3, as shown in FIG. 3. Inlet valve 28 remains in its closed position, while outlet valve 32 moves from its open position to its closed position. Plunger 42 remains at the +169steps of position 48. Control unit 17 measures the distal pressure using distal pressure sensor 34 to determine the final pressure in pump chamber 30 after the outlet valve has closed. Preferably, this measurement is accomplished by monitoring the distal pressure at every valve motor step and determining the final pressure by applying the Average Filter Pressure transform (Equation (1)) to the first eight data samples.

Part 4 begins with inlet valve 28 moving from its closed position to its open position. The plunger moves from the +169 steps extension, at position 48, to home position 44. This full stroke is directly proportional to the volume of medicinal fluid A that is required to be drawn into chamber 30, which in this preferred embodiment is 333 µl. A proximal pressure spike 51 is recorded as inlet valve 28 opens; however, this pressure spike is not used for any compensation calculations relating to the present invention. The timing of the retraction is preferably as quickly as the stepper motor can move the plunger.

At the end of Part 4, the first pump cycle is complete. Any deficiency in the Actual Volume Delivered (calculated in Part 2 as described above) is corrected by changing the timing of the pump cycles, to compensate for any variations between the desired delivery rate and the actual delivery rate. Because cassette type infusion pumps are constant displacement pumps, the delivery rate of the medicinal fluid is changed by changing the number of pump cycles per unit time. Thus, the length of time between pump cycle n and pump cycle n+1 is a function of the desired delivery rate that was programmed into the control unit of the pump, and the actual volume delivered. A higher medicinal fluid delivery rate requires less time between successive pump cycles.

When the control unit has determined that the appropriate amount of time has passed and a new pump cycle is to begin, the process generally described above is repeated for the next pump cycle. The process for the next (second) pump cycle is essentially identical to that described for the first pump cycle; however in this second pump cycle, and all subsequent cycles, instead of using the pressure measured by the proximal pressure sensor in Part 1 as an input to the algorithm to determine the correction position of the plunger, the Distal Suspend Pressure (which corrects for any calibration differences between the distal and proximal pressure sensors) is used, as described in detail above. Thus, pressure compensated plunger positions 46a and 46b for the second and third pump cycles may be different than pressure compensated plunger position 46, which was determined during the first pump cycle. The magnitudes (absolute values) of Distal Pressure Spikes 50a and 50b should be much less than the magnitude of Distal Pressure Spike 50, due to the correction applied. Also, the magnitude of subsequent proximal pressure spike 51a may vary from the value for proximal pressure spike 51 in the first pump cycle.

Figure 4:
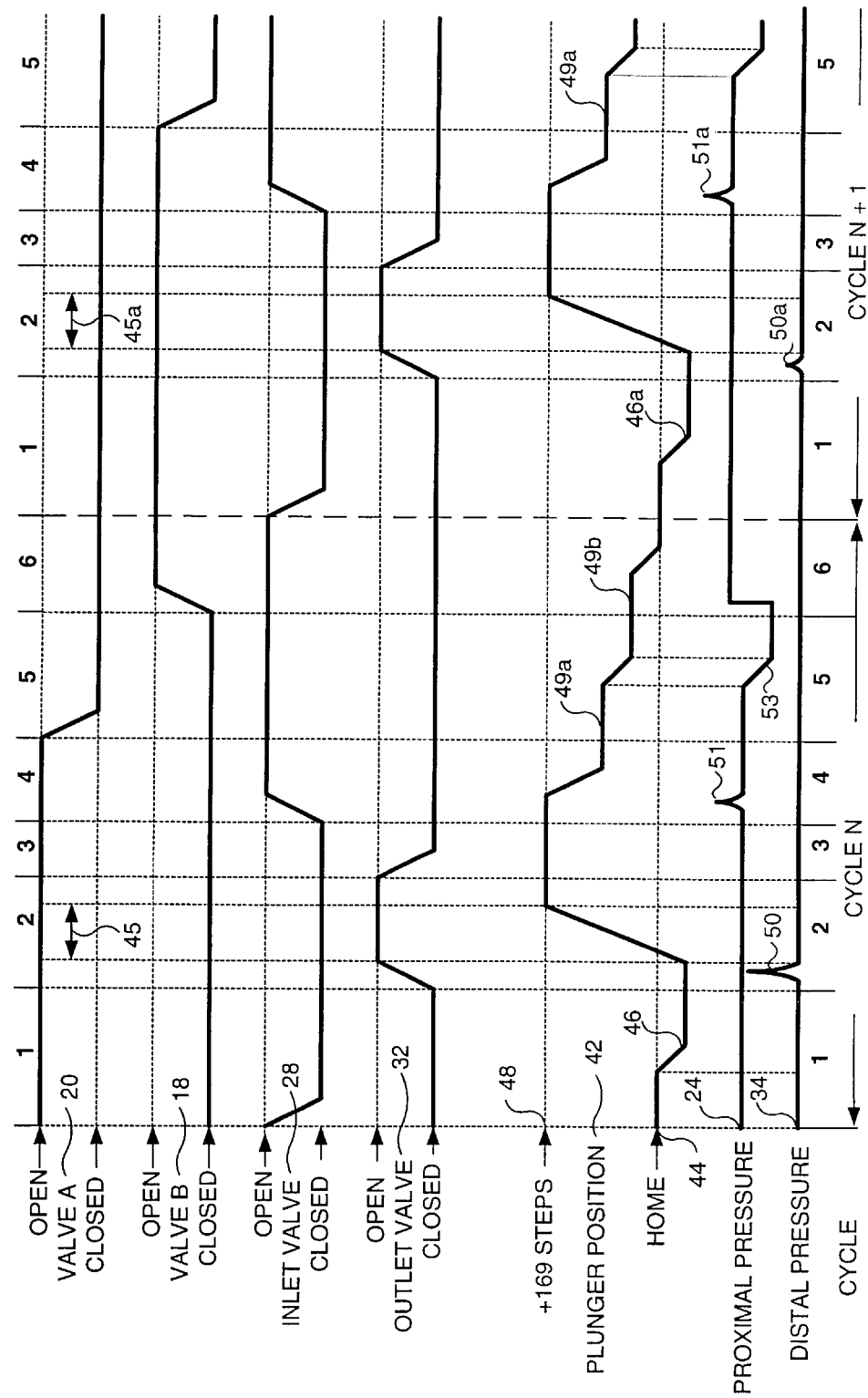
FIG. 4 is a valve cycle diagram for a pressure compensated multi-channel pump, in accord with the present invention.

FIG. 4 illustrates the pump cycle for the multi-channel cassette pump 10 shown in FIG. 1 using both medicinal fluid A from source 12 and medicinal fluid B from source 14. Because medicinal fluid is now being drawn from both fluid sources, a complete pump cycle consists of six parts rather than the four part pump cycle described in connection with FIG. 3. In Part 1, supply valve 20 is in its open position, and supply valve 18 is in its closed position. Inlet valve 28 is initially in its open position and rapidly closes at the beginning of Part 1. Outlet valve 32 is in its closed position and remains in the closed position throughout Part 1. Plunger 42 is initially in its home position 44. At the beginning of Part 1, the microprocessor of control unit 17 uses proximal pressure sensor 24 and distal pressure sensor 34 to measure the pressures at the inlet and the outlet of the pump, respectively. Based on these pressures, the algorithm determines the adjustment required to the position of plunger 42 to compensate for the differential pressure, using the lookup tables based on the data illustrated in FIGS. 5 and 6, in the same manner as has been described above with respect to Part 1 of FIG. 3. Similarly, during Part 1, plunger 42 moves to pressure compensated plunger position 46 in FIG. 4, which represents a retraction of the plunger from the chamber. This retraction of the plunger indicates that the proximal pressure was found to be greater than the distal pressure. If the distal pressure had been greater than the proximal pressure, the plunger would have been advanced toward the chamber, compared to home position 44 of the plunger.

Part 2 in the pump cycle of FIG. 4 starts with the opening of outlet valve 32. As soon as outlet valve 32 opens, Distal Pressure Spike 50 is detected by distal pressure sensor 34. As described above, in future pump cycles, the spike pressure measured for the previous cycle is used by the algorithm to determine a correction for calibration differences of the distal and proximal pressure sensors, and this correction is employed to determine the position of the plunger, i.e., whether the plunger should be either advanced or retracted. When forcing fluid from the chamber, plunger 42 moves from either the advanced or retracted pressure compensated plunger position 46 (as determined by the algorithm) to +169 steps (position 48). Outlet valve 32 remains open throughout Part 2. Time segment 45 is determined using the Equilibration Step Period transform relationship (Equations (8) and (9)) described above in reference to FIG. 3. Also as described above in reference to FIG. 3, the Actual Volume Delivered is computed (Equation (10)).

At the beginning of Part 3 in the pump cycle shown in FIG. 4, outlet valve 32 returns to its closed position. Plunger 42 maintains its extended position at +169 steps, at position 48. Supply valve 20 remains in its open position, while medicinal fluid B supply valve 18 remains closed, for both Parts 3 and 4. Inlet valve 28 remains in its closed position. Control unit 17 measures the distal pressure using distal pressure sensor 34 to determine the final pressure in pump chamber 30 after the outlet valve has closed. Preferably, this measurement is accomplished by monitoring the distal pressure at every valve motor step and determining the final pressure by applying the Average Filter Pressure transform (Equation (1)) to the first 8 data samples.

The major differences between the four part pump cycle described in connection with FIG. 3, and the six part pump cycle of FIG. 4, occur in Parts 4, 5 and 6 of the six part pump cycle. In Part 4, plunger 42 does not fully return to home position 44, but rather to an intermediate position that corresponds to filling chamber 30 with a calculated volume of medicinal fluid A. In Part 5, a Cassette Compliance transform (described in detail below) is used in conjunction with a plunger movement that results in a 1.0 psi pressure change. The values obtained will be used in Part 6 to calculate the Actual Intake Volumes for medicinal fluids A and B. Plunger 42 returns to home position 44, and in doing so, fills chamber 30 with the medicinal fluid B. As will be described in detail below, plunger 42 always returns to home position 44. It is possible that the movement of plunger 42 from the intermediate position of Part 4 (required to fill chamber 30 with the correct volume of medicinal fluid A) to home position 44 will not result in the desired Target Intake Volume for medicinal fluid B (see Equation (13) described below) being delivered to pump chamber 30. Furthermore, the Actual Intake Volume for medicinal fluid A from Part 4 may have been different than the Target Intake Volume due to pressure conditions. Thus in Part 6, the Actual Intake Volumes for medicinal fluids A and B are determined for use with the algorithm in the next pump cycle, so that any deficiencies in either Actual Intake Volumes for medicinal fluids A or B can be made up in subsequent pump cycles.

Part 4 begins with inlet valve 28 moving from its closed position to its open position. The plunger moves from the +169 steps extension, at position 48, to an intake position 49a for medicinal fluid A. This partial stroke is directly proportional to the volume of medicinal fluid A that is required to be drawn into chamber 30, which is calculated using the Plunger Reference Position transforms as discussed below. After the proper volume of medicinal fluid A has entered pump chamber 30, supply valve 20 (for medicinal fluid A) is closed. This step is different than as described above in relation to the four part pump cycle of FIG. 3, because in the four part pump cycle, supply valve 20 was always open, while supply valve 18 (for medicinal fluid B) was always closed. Because the six part pump cycle of FIG. 4 involves both medicinal fluids A and B, supply valves 18 and 20 must cycle on and off during the pump cycle. As with the single fluid four part pump cycle, a proximal pressure spike 51 is recorded as inlet valve 28 opens. As described above, this pressure spike is not used for any compensation calculations relating to the present invention.

It should be noted that an improvement in the accuracy of the delivery rate can be achieved when administering both medicinal fluid A and medicinal fluid B if the intake sequence for the medicinal fluids is alternated. For example, if in a first pump cycle medicinal fluid A is introduced into pump chamber 30, and then medicinal fluid B is introduced into pump chamber 30, in the next pump cycle, medicinal fluid B is preferably introduced into pump chamber 30 first, followed by medicinal fluid A. By alternating the sequence in which a medicinal fluid is first introduced into pump chamber 30, any delivery rate errors that are a function of the order in which medicinal fluids are introduced into pump chamber 30 will be minimized. It does not matter whether the sequence is alternated every other pump cycle, or some other pattern (such as every third, fourth or fifth cycle), as long as medicinal fluid B is introduced into pump chamber 30 first for substantially the same number of pump cycles as medicinal fluid A.

The timing of the plunger retraction is preferably as quickly as the stepper motor can move the plunger. The Plunger Reference Position is the position of plunger 42 required to achieve a medicinal fluid A Target Intake Volume needed for the next pump cycle. The medicinal fluid A Target Intake Volume consists of a nominal target intake and any Extend Deficiency Volume for medicinal fluid A from the previous cycle. As inlet valve 28 is opened, proximal pressure sensor 24 monitors a pressure spike 51. Because this pressure spike is on the proximal side of the pump, it does not affect the delivery rate of the medicinal fluid to the patient, and is therefore is not used by the algorithm to compensate for a differential pressure (as is Distal Pressure Spike 50, discussed above).

Figure 10:
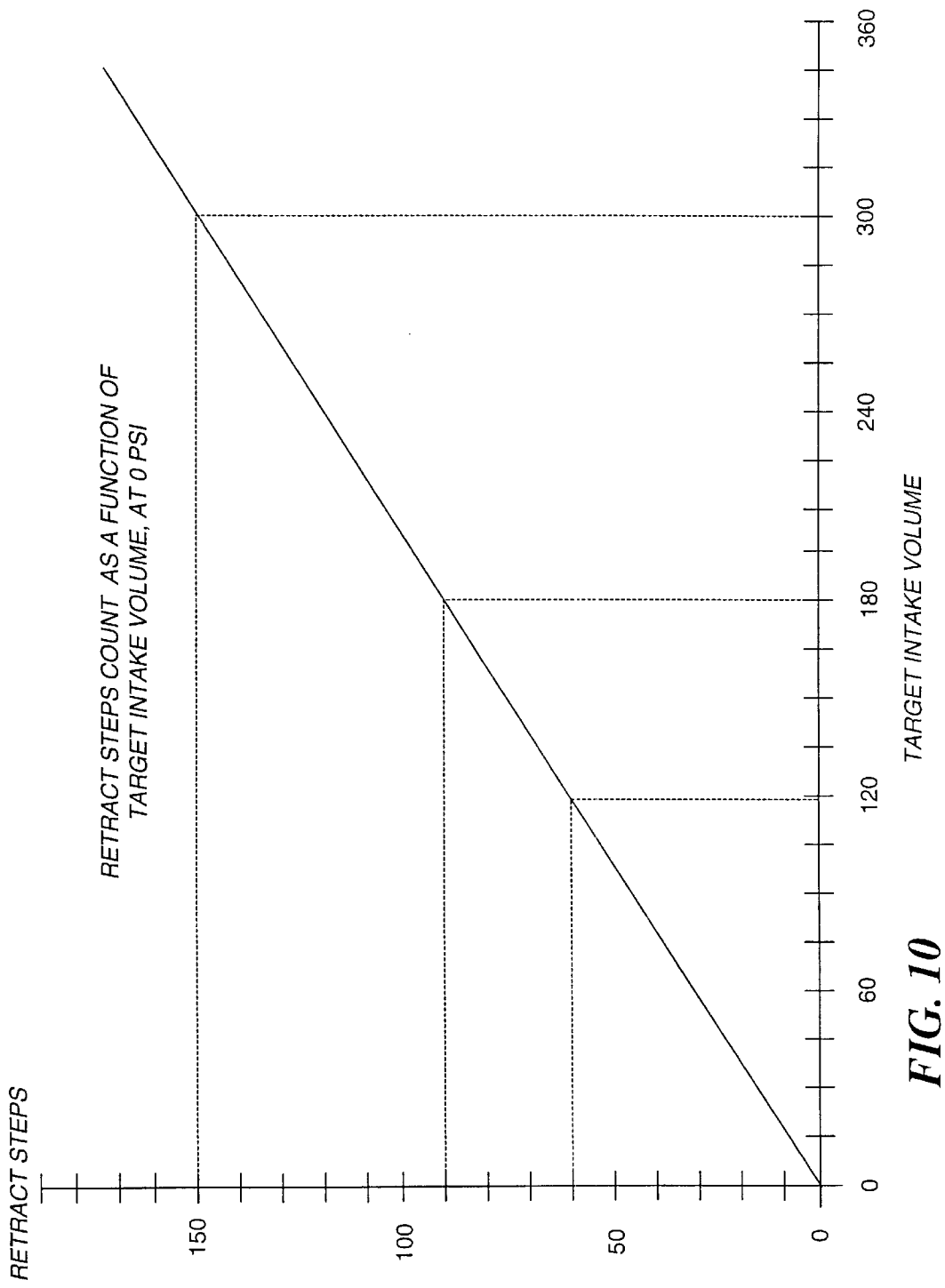
FIG. 10 is a graph showing the driven plunger position as a function of a target intake volume.

The following equation is used to determine the Plunger Reference Position ($X_{Ref}$ relative to +169 steps) needed to deliver the Target Intake Volume ($V_{A\_Tgt}$ and $V_{B\_Tgt}$), for the current cycle (n). The Target Intake Volume consists of a nominal target intake and an Extend Deficiency Volume (see Equations (14) and (15) below) from the previous cycle. There is a plunger Retract Steps lookup table $TAB_{Rtrct}$ (based on the data of FIG. 10), which is a function of Target Intake Volume and is derived empirically. When the first intake is of medicinal fluid A from source 12, the Plunger Reference Position transform is determined from the following equations:

$$X_{Ref} = +169 \text{ steps} - TAB_{Rtrct}(V_{A\_Tgt}) \quad (11)$$

$$V_{A\_Tgt} = \{[(R_{A\_Del}) \div (R_{A\_Del} + R_{B\_Del})](333 \ \mu l)\} - V_{A\_Cum\_Def}(n-1) \quad (12)$$

where:

+169 steps is the nominal plunger extend position;

$V_{A\_Tgt}$ is the Target Intake Volume for medicinal fluid A;

$R_{A\_Del}$ is the user specified delivery rate for medicinal fluid A;

$R_{B\_Del}$ is the user specified delivery rate for medicinal fluid B (in the multi-channel pumping case, see FIG. 4);

333 $\mu l$ is the nominal plunger stroke volume at 0 psig; and $VA_{Cum\_Def}(n-1)$ is the Cumulative Deficiency Volume from the previous cycle for medicinal fluid A.

When the first intake is medicinal fluid A, the Target Intake Volume for medicinal fluid B is defined by the following equation (refer to FIG. 4):

$$V_{B\_Tgt} = 333 \ \mu l - V_{A\_Tgt}. \quad (13)$$

As noted above, , the microprocessor of control unit 17 determines any volume deficiency for the current pump cycle, and adds the deficiency to the Target Intake Volume calculated above. The following equations are used to calculate the plunger Extend Deficiency Volume ($V_{A\_Def}$) and Cumulative Deficiency Volume ($V_{A\_Cum\_Def}$):

$$V_{A\_Cum\_Def}(n) = V_{A\_Cum\_Def}(n-1) + V_{A\_Def}(n) \quad (14)$$

$$V_{A\_Def} = (V_{B\_Int} - V_{B\_Tgt}) - (V_{A\_Int} - V_{A\_Tgt}) \quad (15)$$

where:

$V_{A\_Int}$ is the Actual Intake Volume for medicinal fluid A;

$V_{A\_Tgt}$ is the Target Intake Volume for medicinal fluid A;

$V_{B\_Int}$ is the Actual Intake Volume for medicinal fluid B; and $V_{B\_Tgt}$ is the Target Intake Volume for medicinal fluid B.

As noted above, Part 5 in the pump cycle of FIG. 4 begins (and Part 4 ends) when supply valve 20 moves from its open position to its closed position. Supply valve 18 remains in its closed position, as does outlet valve 32. Inlet valve 28 remains in the open position. A Proximal Reference Pressure is determined using proximal pressure sensor 24 and the Average Filter Pressure transform (Equation (1)). Preferably, the first eight pressure samples are averaged. Plunger 42 is moved from intake position 49a (the Plunger Reference Position calculated in Part 4 for medicinal fluid A) until proximal pressure sensor 24 measures a 1 psi pressure drop 53 at trap 26. As noted above, this known pressure change will be used in conjunction with the Cassette Compliance transform (described below) to calculate a Plunger CM Position (intake position 49b, corresponding to the volume of medicinal fluid B required for the maximum accuracy of the next pump cycle). The movement of plunger 42 from the Plunger Reference Position (intake position 49a) to the Plunger CM Position (intake position 49b) should not exceed 84 steps, or approximately one half of a full stroke of 169 steps. Under ideal operating conditions, a movement of less than 10 steps is normally sufficient. Preferably, if the movement exceeds 84 steps, an alarm will sound to alert a user of an error condition. One possible cause of an error condition would be a leaking cassette. Proximal pressure sensor 24 is then used to determine a Proximal CM Pressure, again using the Average Filter Pressure transform (Equation (1)). The Plunger Reference Position, the Plunger CM Position, the Proximal Reference Pressure, and the Proximal CM Pressure are then used to determine the Cassette Compliance using the Cassette Compliance transform.

Figure 9:
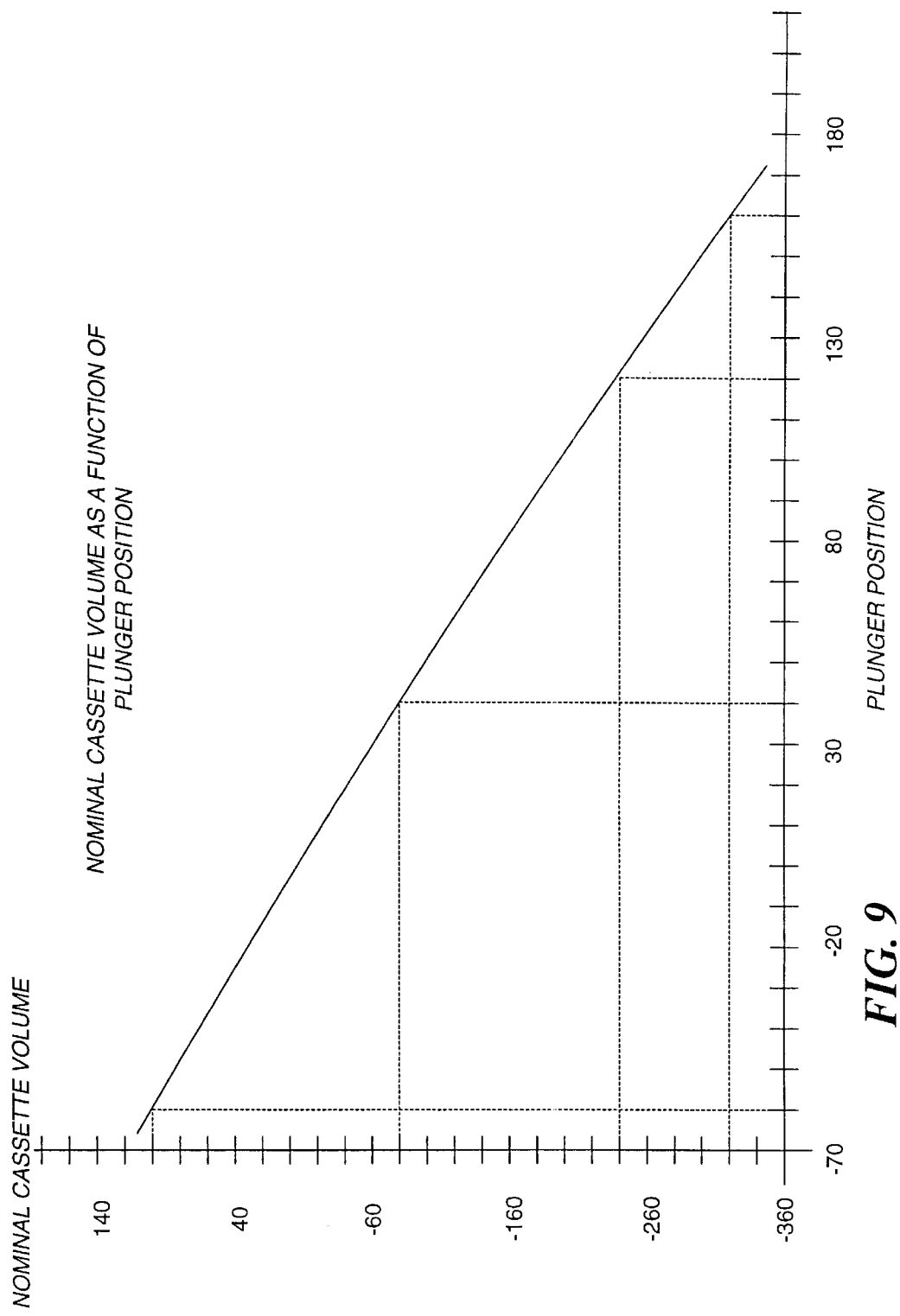
FIG. 9 is a graph showing the nominal cassette volume as a function of the driven plunger position.

The Cassette Compliance is needed to determine the volume of fluid in the cassette as a function of pressure and plunger position. There is a Nominal Cassette Volume lookup table (based on the data of FIG. 9), which is a function of plunger position and is derived empirically. This lookup table is stored in the memory of control unit 17 and is available to the microprocessor when the algorithm is used to compensate for a differential pressure. The Cassette Compliance is a ratio of the change in Nominal Cassette Volumes at two plunger positions and the corresponding change in proximal pressures, as follows:

$$C_{cass} = [TAB_{N\_C\_V}(X_1) - TAB_{N\_C\_V}(X_0)] \div [P_{Px}(0) - P_{Px}(1)] \quad (16)$$

Part 6 of the pump cycle in FIG. 4 begins with supply valve 18 moving from its closed position to its open position. Supply valve 20 remains in its closed position, as does outlet valve 32. Inlet valve 28 remains in its open position. Plunger 42 moves from the Plunger CM Position (intake position 49b for medicinal fluid B), to plunger home position 44. The Actual Intake Volumes for medicinal fluid A and B are computed by applying the Actual Intake Volume transform (described below) as a function of the Plunger Reference Position, the Plunger CM Position, the Distal Suspend Pressure, the Distal PC Pressure, the Proximal Reference Pressure, the Proximal Suspend Pressure, and the Cassette Compliance. At the end of Part 6, the microprocessor of control unit 17 determines any volume deficiency for the current pump cycle, and adds the deficiency to the Target Intake Volume for the next cycle (as described above with respect to Part 4 of FIG. 3). It should be noted that plunger 42 always returns to plunger home position 44, even if such a position results in a less than optimal Actual Intake Volume for medicinal fluid B. Generally, the Actual Intake Volume for medicinal fluid B will represent a deficiency rather than a surplus of medicinal fluid B. This deficiency is recorded and targeted to be corrected in future pumping cycles. When the deficiency is small, it is preferable to accumulate the deficiency over several pump cycles and correct the accumulated deficiency when it exceeds a corresponding plunger position correction of 30 steps. Empirical data have indicated that attempting to correct smaller deficiencies results in lower accuracy.

The following functional relationships are used to calculate Actual Intake Volumes ($V_{A\_Int}$ and $V_{B\_Int}$), for the current pump cycle (n). An intake volume consists of three components: nominal intake, error volume due to distal pressure injection, and error volume due to Cassette Compliance. There will be a Nominal Cassette Volume lookup table, $TAB_{N\_C\_V}$ (based on the data from FIG. 9), which is a function of plunger position and is derived empirically. At the plunger extend position, there is an error volume due to distal injection, which is calculated using the Pumping Chamber Extend Volume lookup table (based on the data of FIG. 7) as a function of the distal differential pressure ($P_{DxSus}+P_{DxPC}$). As the plunger is moved from +169 steps to $X_{Ref}$, there is an error volume due to cassette compliance as a function of proximal differential pressure ($P_{PxRef}-P_{PxSus}$). When the first intake is from medicinal fluid A, source 12, the Actual Intake Volume transform for this source is defined by the following equations:

$$V_{A\_Int}=V_{A\_Nom}+V_{DxInj}+V_{A\_\Delta P} \quad (17)$$

$$V_{A\_Int}=A+[TAB_{Ext\_v}(P_{DxPC})]+[(P_{PxRef}-P_{PxSus})*C_{Cass}] \quad (18)$$

where:

$$A=[TAB_{N\_C\_v}(X_{Ref})-TAB_{N\_C\_v}(+169 \text{ steps})]+ [TAB_{Ext\_v}(P_{DxSus})] \quad (19)$$

$$C_{Cass}=[TAB_{N\_C\_v}(X_{CM})-TAB_{N\_C\_v}(X_{Ref})]+[P_{PxRef}-P_{PxCM}] \quad (20)$$

and where:

$V_{A\_Nom}$ is the nominal intake volume of medicinal fluid A;

$V_{Dxinj}$ is the error volume due to distal infusion at +169 steps;

$V_{A\_\Delta P}$ is the error volume due to Cassette Compliance; and $C_{Cass}$ is the Cassette Compliance between $X_{Ref}$ and $X_{CM}$.

If multi-channel pumping is employed to infuse both medicinal fluids A and B, the following relationships are used:

$$V_{B\_Int}=V_{B\_Nom}-V_{A\_\Delta P} \quad (21)$$

$$V_{B\_Int}=TAB_{N\_C\_v}(0)-TAB_{N\_C\_v}(X_{Ref})]-[(P_{PxRef}-P_{PxSus})*C_{Cass}] \quad (22)$$

where:

$V_{B\_Nom}$ is the nominal intake volume for medicinal fluid B.

The first pump cycle is then complete, and when the microprocessor of control unit 17 determines that a new pump cycle should be initiated (to meet a programmed medicinal fluid delivery rate), the process repeats. For the second cycle, the magnitudes of the pressure compensation at position 46a of the plunger, the duration of time segment 45a, as well as the values of proximal pressure spike 51a and Distal Pressure Spike 50a all can change from the corresponding magnitudes of those elements in the previous pump cycle.

While the preferred embodiment of the invention utilizes both a proximal and a distal pressure sensor, it is contemplated that the present invention can also be applied to increase the accuracy of cassette pumps having only a distal pressure sensor. The actual pressure reading by the distal pressure sensor with the outlet valve of the cassette in its closed position is used for a first distal pressure reading, and then a second distal pressure reading is taken while the outlet valve is opened. Any differential pressure between the first and second pressure readings (corresponding to a chamber pressure and an outlet flow pressure) is then compensated using the algorithm with empirically determined parameters and lookup tables, as described above, to adjust the plunger position at the start of each successive pump cycle. In such a system, the algorithm does not compensate for any differential pressure in the first pump cycle.

Exemplary Summary of the Parts of a Dual Line Pump Cycle

Pumping Cycle Part 1: Equilibrate pumping chamber 30 to the Distal Pressure

Step 1 While closing inlet valve 28, measure the proximal pressure every step and determine the Proximal Suspend Pressure by applying the Average Filter Pressure transform (Equation (1)), on the first eight data samples.

Step 2 Compute the Distal Suspend Pressure by applying the Proximal to Distal Pressure transform (Equation (3)) to the Distal Pressure Spike from the previous cycle.

Step 3 Measure the distal pressure and determine the Distal Deliver Pressure by applying the Average Filter Pressure (Equation (1)) transform.

Step 4 Compute the number of steps to equilibrate the pressure of pumping chamber 30 to the distal pressure by applying the Distal Equilibration Steps (Equations (8) and (9)) transform to the Deliver Distal Pressure and the Distal Suspend Pressure (computed during the previous delivery cycle).

Step 5 Move plunger 42 accordingly.

Pumping Cycle Part 2: Determine the Distal Pressure Spike 50 (to be used in the next cycle), compute the Extend Step Periodfime segment 45, and move plunger 42 to +169 steps position 48.

Step 6 While opening outlet valve 32, sample the distal pressure at intervals of 2 ms/sample for 50 ms.

Step 7 Compute Distal Pressure Spike 50 by applying the Distal Spike Amplitude (Equations (4) and (5)) transform to the Distal Pressure Samples.

Step 8 Compute Extend Step Periodtime segment 45 by applying the Equilibrated Step Period transform (Equations (8) and (9)) as a function of the plunger position, Distal Suspend Pressure, and the Distal PC Pressure from the previous cycle.

Step 9 Move plunger 42 to +169 steps position 48 at Extend Step Period/time segment 45.

Step 10 Compute and report the Actual Volume Delivered (Equation (10)).

Pumping Cycle Part 3: Determine the Distal PC Pressure

Step 11 Initiate closing outlet valve 32, followed by opening inlet valve 28. While closing outlet valve 32, measure the distal pressure every step and determine the Distal PC Pressure by applying the Average Filter Pressure transform (Equation (1)) to the first eight data samples.

Pumping Cycle Part 4: Determine the Plunger Reference. Position and intake a computed Line A Target Intake Volume Step 12 Open inlet valve 28.

Step 13 Calculate Plunger Reference Position 49a needed to get a Line A Target Intake Volume, by applying the Plunger Reference Position transform (Equations (11) and (12)). The Line A Target Intake Volume includes an Extend Deficiency Volume (Equations (14) and (I5)) from the previous cycle.

Step 14 Retract from +169 steps position 48 to Plunger Reference Position 49a.

Step 15 Close supply valve 20 (Line A medicinal fluid).

Pumping Cycle Part 5: Determine the Cassette Compliance

Step 16 Determine the Proximal Reference Pressure by applying the Average Filter Pressure transform (Equation (1)).

Step 17 Move plunger 42, to decrease the proximal pressure at trap 26 by 1.0 psi (pressure drop 53). The movement should not exceed 84 steps from Plunger Reference Position 49*a*. This position is Plunger CM Position 49*b*.

Step 18 Determine the Proximal CM Pressure by applying the Average Filter Pressure transform (Equation (1)).

Step 19 Compute the Cassette Compliance by applying the Cassette Compliance transform (Equation (16)) as a function of Plunger Reference Position and Plunger CM Position, Proximal Reference and Proximal CM Pressures.

Pumping Cycle Part 6: Intake Line B fluid from the Plunger CM to Plunger Home position.

Step 20 Open medicinal fluid B supply valve 18 for Line B.

Step 21 Move plunger 42 to Plunger Home from the Plunger CM Position.

Step 22 Compute the Line A and Line B Actual Intake Volumes by applying the Actual Intake Volume transform (Equations (17) through (22)) as a function of Plunger Reference Position, Plunger CM Position, Distal Suspend Pressure, Distal PC Pressure, Proximal Reference Pressure, Proximal Suspend Pressure, and Cassette Compliance. As noted above, the sequence in which a medicinal fluid is first introduced into pump chamber 30 is preferably alternated, so that medicinal fluid A is introduced into pump chamber 30 first in about as many pump cycles as medicinal fluid B is introduced into pump chamber 30 first.

As discussed above, a preferred embodiment of the present invention will be incorporated in Abbott Laboratories' PLUM A+™ Infusion Pump, which will be used in conjunction with its PLUM™ Cassette; however, a similar algorithm can be empirically determined for other designs of infusion cassettes and infusion pumps. It is envisioned that a particularly efficient combination of algorithm and infusion cassette would be an embodiment in which a single pressure sensor was incorporated into the pumping chamber itself. A functional requirement of the algorithm is that the pressure within the pumping chamber be known at various parts of the pump cycle. Because the existing PLUM™ Cassette includes a proximal pressure sensor and a distal pressure sensor, but not a pressure sensor within the pumping chamber, the algorithm described in detail above uses the pressure readings of the proximal and distal pressures, with the pump valves in the appropriate positions, to approximate the pressure within the pumping chamber at various times in the pump cycle. As described above, a correction may be required due to potential calibration differences between the proximal and distal pressure sensors. Use of a single pressure sensor within the pumping chamber would eliminate the need for such a correction, thus simplifying the algorithm. Depending on the other functional requirements of the infusion cassette, proximal and distal pressure sensors may or may not be required. Thus, it is envisioned that the algorithm could be adapted to accommodate an infusion cassette with proximal, distal and pumping chamber pressure sensors, as well as an infusion cassette with only a pumping chamber pressure sensor.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A pump employed to infuse a fluid flowing from a source into a patient, comprising:
   (a) a disposable cassette having a housing that defines a fluid path from an inlet port that is adapted to couple in fluid communication with the source, to an outlet port that is adapted to couple in fluid communication with an infusion site on the patient, said fluid path including:
      (i) a chamber covered by an elastomeric membrane that when forced into the chamber, displaces the fluid from the chamber through the outlet port, said chamber including a pressure sensor that produces a signal indicative of a pressure in the chamber
      (ii) an inlet valve controlling flow of the fluid into the chamber from the inlet port, said inlet valve being open as fluid flows into the chamber from the inlet port and closed as the fluid is displaced through the outlet port; and
      (iii) an outlet valve controlling flow of the fluid from the chamber toward the outlet port, said outlet valve being open when the fluid is displaced through the outlet port and closed as the fluid flows into the chamber from the inlet port;
   (b) a drive unit adapted to couple with disposable cassette and including at least one prime mover and a plunger, said at least one prime mover moving the plunger relative to the chamber to deform the elastomeric membrane, thereby displacing fluid from the chamber toward the outlet port, said drive unit also actuating the inlet valve and outlet valve to open and close said valves; and
   (c) a control unit, coupled to receive the signals from the pressure sensor, and coupled to the drive unit to control said at least one prime mover and thereby controlling movement of the plunger, said control unit determining a differential pressure from the signals produced by the pressure sensor and adjusting an initial position of the plunger relative to the chamber before the plunger displaces the fluid from the chamber, to compensate for the differential pressure, so that an accuracy of the pump in infusing the fluid into the patient is substantially improved.

2. A method for determining a difference between a targeted intake fluid volume and an actual intake fluid volume in an infusion pump employed for infusing a fluid into a patient, comprising the steps of:
   (a) providing a cassette having a housing that defines a fluid path between an inlet port adapted to couple in fluid communication with a source and an outlet port adapted to couple in fluid communication with an infusion site on the patient, said fluid path including:
      (i) a chamber covered by an elastomeric membrane that when forced into the chamber by a driven member displaces the fluid from the chamber through the outlet port;
      (ii) an inlet valve controlling a flow of the fluid into the chamber from the inlet port, said inlet valve being open as the fluid flows into the chamber from the inlet port and closed as the fluid is displaced through the outlet port;
      (iii) a pressure sensor that produces a signal indicative of a pressure in the chamber; and
      (iv) an outlet valve controlling a flow of the fluid from the chamber toward the outlet port, said outlet valve being open when the fluid is displaced through the outlet port and closed as the fluid flows into the chamber from the inlet port;

(b) opening the inlet valve while the outlet valve is closed, and while the inlet valve is open, moving the driven member to a first position such that the elastomeric membrane adjusts a volume of the chamber to correspond to the targeted intake volume, thus filling the chamber with fluid;

(c) determining a first pressure in the pumping chamber using the pressure sensor;

(d) moving the driven member to a second position such that the elastomeric membrane is forced into the chamber, thus decreasing the volume of the chamber, the pressure sensor determining a second pressure in the pumping chamber that exceeds the first pressure by a predetermined amount;

(e) determining the actual intake fluid volume as a function of the first pressure, the second pressure, the first position of the driven member, and the second position of the driven member; and (f) determining a difference between the targeted intake fluid volume and the actual intake fluid volume.

3. A method for determining a difference between a targeted delivery fluid volume and an actual delivery fluid volume in an infusion pump employed for infusing a fluid into a patient, comprising the steps of:

(a) providing a cassette having a housing that defines a fluid path between an inlet port adapted to couple in fluid communication with a source and an outlet port adapted to couple in fluid communication with an infusion site on the patient, including an outlet pressure sensor that produces a signal indicative of a pressure proximate the outlet port, said fluid path including:

(i) a chamber covered by an elastomeric membrane that when forced into the chamber by a driven member displaces the fluid from the chamber through the outlet port;

(ii) an inlet valve controlling a flow of the fluid into the chamber from the inlet port, said inlet valve being open as the fluid flows into the chamber from the inlet port and closed as the fluid is displaced through the outlet port; and (iii) an outlet valve controlling a flow of the fluid from the chamber toward the outlet port, said outlet valve being open when the fluid is displaced through the outlet port and closed as the fluid flows into the chamber from the inlet port;

(b) opening the outlet valve while the inlet valve is closed, and while the outlet valve is open, determining a first pressure proximate the outlet port using the outlet pressure sensor;

(c) moving the driven member to a first position such that the elastomeric membrane reduces a volume of the chamber to correspond to the targeted delivery volume, thus emptying the chamber of fluid;

(d) determining a second pressure proximate the outlet port using the outlet pressure sensor;

(e) closing the outlet valve while the inlet valve is still closed, and then opening the inlet valve while the outlet valve is closed;

(f) while the inlet valve is open, moving the driven member to a second position such that the elastomeric membrane expands a volume of the chamber to correspond to the targeted delivery volume, thus filling the chamber with fluid;

(g) determining the actual delivery fluid volume as a function of the first pressure proximate the outlet port, the second pressure proximate the outlet port, the first position of the driven member, and the second position of the driven member; and (h) determining a difference between the targeted delivery fluid volume and the actual delivery fluid volume.

4. A method for adjusting at least one parameter of an infusion pump for infusing a fluid into a patient, to maintain an accurate delivery of the fluid, compromising the steps of:

(a) providing a cassette having a housing that defines a fluid path between an inlet port adapted to couple in fluid communication with a source and an outlet port adapted to couple in fluid communication with an infusion site on the patient, said fluid path including a chamber from which fluid is displaced through the outlet port;

(b) monitoring at least one of an inlet pressure proximate the inlet port and an outlet pressure proximate the outlet port;

(c) providing a drive unit adapted to couple with the cassette and including a plunger that displaces the fluid from the chamber through the outlet port;

(d) determining an adjustment to an initial position of the plunger relative to the chamber before the plunger displaces the fluid from the chamber, to compensate for a differential pressure between the inlet pressure and the outlet pressure;

(e) changing a position of the plunger relative to the chamber before the plunger begins to displace the fluid from the chamber, in accord with the adjustment to the initial position determined in the preceding step;

(f) determining an actual volume of fluid delivered in a current pump cycle;

(g) determining a change in a duration of a delivery stroke of the plunger required to compensate for any difference between the actual volume of fluid delivered and a desired volume of fluid to be delivered;

(h) applying a change in the duration of the delivery stroke during the next pump cycle; and wherein the step of determining the change in the duration of a delivery stroke comprises the steps of:

(1) using lookup tables to determine a plunger extend position as a function of an outlet differential pressure, and an error volume at a plunger home position as a function of the inlet pressure; and (2) determining the duration of the delivery stroke in the next pump cycle required to maintain a desired delivery rate as a function of a time when a previous extend stroke was completed, a time a current extend stroke began, a nominal stroke volume, a user specified delivery rate, a nominal extend stroke position, a plunger corrected position prior to the extend stroke, the plunger extend position, and the error volume.

5. A pump employed to infuse a fluid flowing from a source into a patient, comprising:

(a) a disposable cassette having a housing that defines a fluid path from an inlet port that is adapted to couple in fluid communication with the source, to an outlet port that is adapted to couple in fluid communication with an infusion site on the patient, and including an inlet pressure sensor that produces a signal indicative of a pressure proximate the inlet port, and an outlet pressure sensor that produces a signal indicative of a pressure proximate the outlet port, said fluid path including:

(i) a chamber covered by an elastomeric membrane that when forced into the chamber, displaces the fluid from the chamber through the outlet port;

(ii) an inlet valve controlling flow of the fluid into the chamber from the inlet port, said inlet valve being open as fluid flows into the chamber from the inlet port and closed as the fluid is displaced through the outlet port; and (iii) an outlet valve controlling flow of the fluid from the chamber toward the outlet port, said outlet valve being open when the fluid displaced through the outlet port and closed as the fluid flows into the chamber from the inlet port;

(b) a drive unit adapted to couple with the disposable cassette and including at least one prime mover and a plunger, said at least one prime mover moving the plunger relative to the chamber to deform the elastomeric membrane, thereby displacing fluid from the chamber toward the outlet port, said drive unit also actuating the inlet valve and outlet valve to open and close said valves; and (c) a control unit, coupled to receive the signals from the inlet pressure sensor and the outlet pressure sensor, and coupled to the drive unit to control said at least one prime mover and thereby controlling movement of the plunger, said control unit determining a differential pressure from the signals produced by the inlet pressure sensor and the outlet pressure sensor and adjusting an initial position of the plunger relative to the chamber before the plunger displaces the fluid from the chamber, to compensate for the differential pressure, so that an accuracy of the pump in infusing the fluid into the patient is substantially improved.

6. The pump of claim 5, wherein the adjustment to the initial position of the plunger changes a pressure of the fluid in the chamber before the outlet valve is opened to enable the fluid to be displaced from the chamber.

7. The pump of claim 5, wherein as a function of the adjustment to the initial position of the plunger, the control unit changes a duration of time for the fluid to be displaced from the chamber by the plunger.

8. The pump of claim 5, wherein the plunger is always in contact with the elastomeric membrane during the pump cycle.

9. The pump of claim 5, wherein said differential pressure is less than 0.5 psi, after being compensated.

10. The pump of claim 5, wherein the control unit includes a processor coupled to a memory in which machine instructions comprising a control algorithm are stored, said machine instructions being executed by the processor and causing it to determine the differential pressure and to adjust the initial position of the plunger to compensate for the differential pressure.

11. The pump of claim 10, wherein the control algorithm uses a pressure sensed by the outlet pressure sensor, after the outlet valve has just opened and fluid is flowing through the outlet valve to the patient, to determine a calibration difference between the inlet pressure sensor and the outlet pressure sensor, and wherein said calibration difference is used by the algorithm when adjusting the initial position of the plunger to compensate for the differential pressure during a next pump cycle.

12. The pump of claim 10, wherein parameters of the control algorithm are empirically determined for a specific design of the disposable cassette and the drive unit.

13. The pump of claim 10, wherein when the control unit determines that the differential pressure between the inlet pressure sensor and the outlet pressure sensor is such that a greater pressure is indicated at the outlet pressure sensor than at the inlet pressure sensor, the control unit causes the plunger to advance toward the chamber to a position determined by the algorithm, and when the control unit determines that the differential pressure between the inlet pressure sensor and the outlet pressure sensor is such that a lower pressure is indicated at the outlet pressure sensor than at the inlet pressure sensor, the control unit causes the plunger to retract away from the chamber, to a position determined by the algorithm.

14. The pump of claim 13, wherein when the plunger is advanced from its initial position to a compensated position as determined by the algorithm, said advancement causes a greater deformation of the elastomeric membrane, and thus causes a volume of the chamber to decrease and a pressure within the chamber to increase; and wherein when the plunger is retracted from its initial position to a compensated position as determined by the algorithm, said retraction causes a lesser deformation of the elastomeric membrane, and thus causes a volume of the chamber to increase and a pressure within the chamber to decrease.

15. The pump of claim 10, wherein the algorithm incorporates a first lookup table in which the plunger position is a function of a pressure associated with the inlet, and a second lookup table in which the plunger position is a function of a pressure associated with the outlet, and a compensated plunger position is determined by combining a result from both lookup tables.

16. The pump of claim 15, wherein the first and second lookup tables are empirically determined.

17. The pump of claim 10, wherein after the plunger has exerted a force on the elastomeric membrane and displaced the fluid from the chamber to the outlet port, the control unit uses the algorithm to determine the actual fluid volume displaced from the chamber, and to then determine a correction factor for modifying the next pump cycle to maintain a desired delivery rate of the fluid to the patient.

* * * * *